US005573915A

United States Patent [19]
Barry, III et al.

[11] Patent Number: 5,573,915
[45] Date of Patent: Nov. 12, 1996

[54] DETERMINING THE ABILITY OF A COMPOUND TO INHIBIT THE CYCLOPROPANATION OF MYCOLIC ACIDS IN PATHOGENIC MYCOBACTERIA

[75] Inventors: Clifton Barry, III, Hamilton; Ying Yuan, Missoula, both of Mont.

[73] Assignee: United States of America, Washington, D.C.

[21] Appl. No.: 457,245

[22] Filed: Jun. 1, 1995

[51] Int. Cl.⁶ .............................. C12Q 1/68; C12N 9/00
[52] U.S. Cl. ............................................ 435/6; 435/183
[58] Field of Search ........................................ 435/183, 6

[56] References Cited

PUBLICATIONS

Wheeler et al. Letters in Applied Microbiolgy 17(1):33–36(1993).
Banerjee, A. et al., Science 263, 227 (1994).
Beera, G. S., Minnikin, D. E., Wheeler, P. R., Ratledge, C., Chem. Phys. Lip. 66, 23(1993).
Daffe, M., Lanelle, M. A., Lacave, C., Res. Microbiol. 142, 397 (1991).
Eiglmeier, K., Honore, N., Woods, S. A., Caudron, B., Cole, S. T., Mol. Micro. 7, 197 (1993).
Goren, M. B., Bacteriol. Rev. 36, 33 (1972).
Grogen, D. W. and Cronan, J. E. Jr., J. Bact. 158:286 (1984).
Minnikin, D. E. in The Biology of the Mycobacteria, C. Ratledge, and J. Stanford, Eds. (Academic Press, San Diego, CA, 1982), pp. 95–184.
Qureshi, N., Takayama, K., Schones, H. D., J. Biol. Chem. 255, 182 (1980).
Snider, D. E. Jr., and Roper, W. L., New England J. of Med. 326, 703 (1992).
Takayama, K., and Qureshi, N. in The Mycobacteria: A Sourcebook, Park A, G. P. Kubica and L. G. Wayne, Eds (Marcel Dekker, Inc., New York, NY, 1984).
Takayama, K., Qureshi, N., and Schnoes, H. K., Lipids 13, 575 (1978).
Takayama, K., Wang, L. David, H. L., Antimicrob. Agents Chemoth. 2, 29 (1972).
Wheeler, P. R., Beera, G. S., Minnikin, D. E., Ratledge, C. Biochim. Biophys. Acta 1167, 182 (1993).
Winder, F. G. in The Biology of the Mycobacteria, C, Ratledge, and J. Stanford, Eds. (Academic Press, San Diego, CA 1982), pp. 353–438.
Taylor, F. R. and Cronan, J. E. Jr., Biochemistry 15:3292 (1979).
Thole, J. E. R., Keulen, W. J., Kolk, A. H. J., et al., Infect. Immun. 55:1466–1475.
Garbe, T. R., Barathi, Jaya, Barnini, Simona, et al., Microbiology (1994) 140:133–138.

Primary Examiner—W. Gary Jones
Assistant Examiner—Ethan Whisenant
Attorney, Agent, or Firm—Townsend and Townsend and Crew,; Guy W. Chambers

[57] ABSTRACT

DNA and protein compositions useful for both diagnosis and design of therapeutics for treatment of tuberculosis and other mycobacterial infections. More specifically, the present invention relates to DNA and protein compositions which are responsible for the cyclopropanation of mycolic acids in M. tuberculosis and other pathogenic forms of mycobacterium. A method for determining the ability of a compound to inhibit the cyclopropanation of mycolic acids in pathogenic mycobacteria is disclosed.

4 Claims, 8 Drawing Sheets

```
DNASIS
MULTIPLE EDIT1
                      10         20         30         40         50         60
M.tuberculo     1  M-------   --PDELKPHF ANVQAHYDLS DDFFRILDP  TQTYSCAYFE RDDMTLQFAQ   60
M.leprae        1  MVPSQSHPAK TPRKQLKPPI EAVQSHYDRS NEFFKLWLDP SMTYSCAYFE RPDLTEEEAQ   60
E.Coli          1  ARLFNLQSKK RA-------W IVGKEHYDLG NDLFSRMLDP FDYSCAYWK  DAD-NLESAQ   60

70         80         90        100        110        120
M.tuberculo    61  IAKIDLALGK LGLQPGMTLI DVGCGWGATM MRAVEKYDVN VVGLTLSKNQ ANFIVQLVAN  120
M.leprae       61  RAKRDLAISK LGIEPGMTLI DIGCGWGSTM LHAIEKYDVN VLGLTLSANQ LAHNKLKFAE  120
E.Coli         61  QAKLKMICEK LQLKPGMRVL DIGCGWGGLA HYMASNYDVS VVGVTLSAFQ QKMAQERCEG  120

130        140        150        160        170        180
M.tuberculo   121  SENIRSKR-- -VLIAGWEQF DEPVDRIVSI ------GAFEHF GHERYDA    FFSLAHRLP  180
M.leprae      121  IDHTRTDRTK DVRLQGWEQF DEPVDRIVSL GAFEHFADGA GDAGFERYDS EFKMCYDVLP  180
E.Coli        121  LDVI------ -ILLQDYRDL NDQFDRIVSV GMEH--     -VGPKNYDT  YEAVVDRNLK  180

190        200        210        220        230        240
M.tuberculo   181  ADGVMLLHTI TGLHPKEIHE RGIPMSFTFA RFLKFIVTEI FPGGRLPSIP MVQECASANG  240
M.leprae      181  DDGRMLLHTI IVPDAKETKE LGLTTPMSLL RFIKFILTEI FPGGRLPKIS QVDHYSSNAG  240
E.Coli        181  PEGIFLLHTI ------GSKK TDLNVDPWIN KY------I  EPNGCLPSVR QTAQ-SSEPH  240

250        260        270        280        290        300
M.tuberculo   241  FTVIRVQSLQ PHYAKTIDIW SAAIQANKGQ AIALQSEVY  ERYMKYLTGC AFMFRIGYID  300
M.leprae      241  FTVERYFRIG SHYVPTLNAW AAAIEAHKDE AIALQGRQIY DTYMHYLTGC SDLFR-----  300
E.Coli        241  FVMEDWHNFG ADYDTTLMAW YERFLAWPE  IADNYSERFK RMFTYYLNAC AGAFRARDIQ  300

310        320        330        340        350
M.tuberculo   301  VNQ-FTC--- ----QK*
M.leprae      301  ---DRYIDVC QFTLV--K..
E.Coli        301  LWQVVFSRGV ENGLRVAR..
```

FIG. 2

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
  ( A ) LENGTH: 5100 base pairs
  ( B ) TYPE: nucleic acid
  ( C ) STRANDEDNESS: single
  ( D ) TOPOLOGY: linear ( i i ) MOLECULE TYPE: DNA (genomic)

( v i ) ORIGINAL SOURCE:
  ( A ) ORGANISM: Mycobacterium tuberculosis ( i x ) FEATURE:
  ( A ) NAME/KEY: misc_feature
  ( B ) LOCATION: 521..1381
  ( D ) OTHER INFORMATION: /product="cma"

( i x ) FEATURE:
  ( A ) NAME/KEY: misc_feature
  ( B ) LOCATION: 1388..2539
  ( D ) OTHER INFORMATION: /product="ORF2"

( i x ) FEATURE:
  ( A ) NAME/KEY: misc_feature
  ( B ) LOCATION: 4158..5027
  ( D ) OTHER INFORMATION: /product="ORF3"

( x i ) SEQUENCE DESCRIPTION: SEQ ID NO:1:

```
GGATCCACCC  GGATGTTCCA  TTCGGTGATC  GGCTGGCCGT  CGAACATGCC  GCCCATGATC        60

ACCAGCCGGC  GCAGCAGCCT  CGGCAGCGCG  GGTTCGGCGC  GCAGCAGCGC  CAGGTTGGTC       120

AGCGGGCCGG  TGACCAGACC  GATCAGGTCG  CCGGCGTGGG  AGTGCGCCGC  CGCGATCCAG       180

GCCGTCGTGG  CGTCATAATC  GGTGAGCCGG  CGATTGCTGG  CCGGCAGCTC  GGCATAGCCT       240

ATCCCCTTGG  GGCCGTGAAA  CTTTGGGTGA  TCGGGCCACC  GGCCGCCGAG  CGGCTCATCG       300

GCGCCTTTGG  ACACGGGGAT  GTCTGCGGCA  CCGCACAATT  CGAGCAAGCT  CAGGTTGTTC       360

GCGCACACTT  GACCTACCGC  GATGTTTCCG  CCGGTCGAGG  CGATGCCGAC  CAGATCGGCG       420

TCGGGACTGG  CCAGCAGATA  GATCACGGCC  AGCGCGTCGT  CGATGCCGGT  GTCGACGTCG       480

GCGAATACGA  CGCTCACCGC  GACGACGATA  CGCTATCCCA  ATGCCCGACG  AGCTGAAGCC       540

GCACTTCGCC  AACGTGCAGG  CGCACTACGA  CCTGTCCGAC  GACTTCTTCC  GGCTGTTCCT       600

CGATCCCACT  CAGACCTACA  GCTGCGCCTA  CTTCGAGCGC  GACGACATGA  CGCTGCAAGA       660

GGCGCAGATC  GCCAAGATCG  ATCTCGCGCT  GGGCAAACTC  GGATTGCAGC  CGGGCATGAC       720

ACTGTTGGAC  GTCGGCTGCG  GCTGGGGCGC  CACCATGATG  CGCGCGGTGG  AAAAATACGA       780

CGTCAACGTC  GTCGGTCTGA  CCCTGAGCAA  AAACCAGGCC  AACCACGTTC  AGCAGCTGGT       840

CGCCAACTCC  GAAAATCTAC  GCTCCAAACG  CGTTCTGCTG  GCCGGCTGGG  AACAGTTTGA       900

CGAGCCCGTC  GACCGCATCG  TCAGCATCGG  TGCTTTCGAA  CATTTCGGTC  ACGAGCGCTA       960
```

```
CGACGCGTTC TTCAGCCTGG CGCATCGCCT GCTGCCCGCT GACGGGGTCA TGCTGCTGCA    1020
CACCATCACC GGGTTGCATC CGAAAGAGAT CCACGAACGC GGCCTGCCCA TGTCGTTCAC    1080
CTTCGCTCGT TTCCTGAAAT TCATTGTGAC CGAGATCTTT CCGGGTGGGC GGCTGCCCTC    1140
GATACCGATG GTGCAGGAGT GTGCCAGCGC AAACGGCTTC ACCGTCACCA GAGTTCAATC    1200
GTTGCAGCCG CACTATGCGA AAACCCTCGA CCTCTGGTCC GCGGCGTTGC AGGCCAACAA    1260
GGGCCAGGCC ATCGCGCTGC AATCCGAGGA AGTCTACGAG CGGTATATGA AGTACCTCAC    1320
CGGCTGCGCC GAGATGTTTC GCATCGGATA CATCGACGTC AACCAGTTCA CCTGCCAGAA    1380
GTGACTACCA ATGCACACCG GGCACCAGTC GCCCCAAGCG CCTGAGCGGC CTCGGGACTC    1440
CCGCGCGGGC GGATCGCCGG GGACGCCGCG GCGCCGGTGG GCGGTCCGCG TCTGGACGCG    1500
AAATCCCCTG CGCTGCAGCT GAATCGGGAT AGCCCAGATA GAGCTGGTGC AGAATTCGGC    1560
GCGACAGCCG TGGCGCGACG TAGTTGCCGG CTTCGGCGAG CGTACCCAAC GGAGTGTCGA    1620
TGCGCGCCGG CTTTTCCACG AGTCCGCGGA TCACCATCGC CGCCGCGCGT TCGCGGCTGA    1680
TCGCGCGCAC CGGGTTGAGC CGCCGCGACG GCACGATCAT CGGGGTGGCC ACCAGCGGCA    1740
TATGGATGTT GGTGAACGTG ATGTGGTCGG ACAGCGTCTC GGAGGCGACC ACGTCGGCGA    1800
ACGCGTCCAG CGCGGCCTTG GTGGGCAGAT ACGAGCTGTA CTTGGGATTG CGGGCCTGCA    1860
CGCCGGCGCT GGAGACGTTG ACGACGTGGC CGAACCGGCG CTCGCGCCAA TGCGGCAGCA    1920
GCGCCAGCAC CATGCGCACC GCGCCGAAGT AGTTGACCGC CATCACCCGC TCGTAGTCGT    1980
GCAGCCGGTC GGTGGAGTTG ACCACCGAGC GGCGTATCGA CCGGCCGGCG TTGTTCACCA    2040
GGTAGTCCAC GTGGTCGAAA CGGCCCAGGA TGTCCTTGAC GGTGTGCTCC ACCGACGCGG    2100
AATCGGTGAC GTCGCAGGTG AATGCGTGCG CCTGACCGCC ATGGGCGCGG ATCTCGGTGA    2160
CCAGCTCATC TAGCGCGTTG CCGTTGCGGG CCAGCGCGAA TACCGTCGCA CCCCGTTTGG    2220
CGACGGCGAT CGCCGATGCC CTCCCGATGC CGCTGGACGC ACCGGTGATG ATGACGTGGC    2280
GGCCCAGCAG CGGATCGTTG CGACGCGCGC GGTCGGGGTC GAGGTGCTCG GCCCAATACC    2340
GCCACAGCCC GGGCGCGTAG GTGGCGAATT CGGGGACGTG AATGCCGGTG CCGCGCAACG    2400
CTTCCCGGGT TGTGTCGGAC GTGAACGTGG GCGCGCAGCC GACGACGTCG AAAATCTCGG    2460
CGGGAATTCC CAGTTGGGTG GCCGCCATGT TGCGCAGCAC CTTGGCGCGG CCGCGCGCGT    2520
TGAGCACCGG TGCGGCCACA AAGCCGGGCA GCGTCCCGAG TAGCGGGGGC AGTCGGCCGC    2580
GCCGGCGATC CCGCGGTAGA TGCCGCGCAG TCCGATTGCT GTCGGCGCGG TCAAATGAAA    2640
CGTCTGCCCA TCCCGGCCGT CGGCGTGCAT GAGCGCCACC AGCGCGTCGG CCACATAGTC    2700
GACCGGCACG ATGTTGGTGC GCCCAATGTC CGGCAGCAGC ATCGGGGTGA ACGACGGCAA    2760
CACCGCCAGC TTGGCCAGCA CCCCGAACAA GTAGTAGGGT CCGTCGATCG TGTCCATCTC    2820
GCCGGTGCGC GAATCACCCA CCACCACGCC GGGCGGTAGA TGCGATAGCG CAGGCCGGGC    2880
GTGGAGCGCA CCACGCGTTC GGCCTCGAAT GTCATCCGAT GATACGGGGT CGGTAGGCGC    2940
TGGCCGACGT CGAAGTCGGC CTCGGTGTAG TGGCCGGCGA AGTCTCCGGC CACCGCGATC    3000
GACGACACGT GATGAAACGT GGCGTCAAGG TGCCGCCAGC TCGATGACGG CGCGGGTGGC    3060
GTCGGCCCAG GTGGTGTCGT GTACCGCCGC ACAGTGCAGC ACATGGTCGA TATCGCCTAG    3120
CTCGGCGATG GTCCGCTCGG ACAGTTCGAG CTCCGTGAGA TCACCGACCA GCGGTCTTAC    3180
CCGGTCACCC CACTGGCCGG CGAGGCGCTC GAAGCGGCTT AACGACTGGC GGCGAACCAG    3240
CGCCCACAGC CGTGCCTCGG GTCGGCCGTC CAGGAGACGG GATACCACGT GGCGCCCGAT    3300
AAACCCGGTA CCGCCGGTAA CGACGTACCG CATGCGGTCA ATCGTGGCGG TCAGCGGCGG    3360
```

| | | | | | | |
|---|---|---|---|---|---|---|
| TAAGCGTCAA | CCGCGCGGTC | AGGTGAAGTT | ACGGATGCCG | TCCCATTCCA | CCAGCCTCCA | 3420 |
| GCCGGTCACT | GGGTTGCCGG | TGATCACCAC | GCGGCCGATG | TTGGGCAGTG | GATGGGTGGT | 3480 |
| CAGCAGGCTG | TCCCTAGAGT | TTCGTGCGTT | CATCAGCGTC | CAGATCATGA | TCGCTACCCC | 3540 |
| CTGCGAGAAC | ACGAACCGGC | GTATTGTGGC | CGCTGTCGTA | GATCTTGCGG | ACGGCGGCGC | 3600 |
| TGAACTGGGA | ATTGAATTCG | GTGCCGCTGA | TCGACCCCGG | AATAGTGTTG | TGAACATCGC | 3660 |
| CGGCCAGCCA | GTCTGCCGGT | GCCAGCATAT | ATGTTGAGTT | GGCCATTGAT | TCGGGTTTCC | 3720 |
| CGTTGAACCA | GCCGGCCTTG | ATCGCTTGCT | GGCCCGGAAG | AATCTCGACT | TGCTTGCCAA | 3780 |
| GTTCGCCGGC | CAACGGCCCG | GCGGTCTGCT | GGTCGGCCGC | CATGGGGGAG | GAATAGATGC | 3840 |
| TGTCGACATC | TCTGCGGGAA | ACCTGGTGCG | CGACCTGCTG | CGCCTCTGCT | TTGCCGTCGG | 3900 |
| CGCTGAGGCC | GGAACCGGGC | ATGTCGGTGT | CGATGATCCC | GTCGGCGTTG | GCCTGGGATT | 3960 |
| GCGCGTTGCG | ATAAAGGTCA | AGGTGATGCT | GCGTGGCTGC | GTGGGACCGC | CGCAGGCGAG | 4020 |
| GAGTAGCGTC | GCGGCGAGCA | CGGCTAGAAC | TGTGCAGGCC | TTCCGGACCG | GGGTTCGCTT | 4080 |
| CGCCATGGCG | ATAGCTGCCC | TGTCGATACC | GTCCGGGGGA | AGGGCTTGCA | TGATTTTCCA | 4140 |
| ACCGGGAGGA | GAGTTGCATG | GCGATTGATC | CGAACTCCAT | AGGTGCAGTG | ACCGAGCCGA | 4200 |
| TGTTGTTCGA | GTGGACCGAC | CGGGACACGC | TGCTTTACGC | GATCGGGGTG | GGCGCCGGGA | 4260 |
| CCGGAGATCT | GGCGTTCACC | ACGGAGAACA | GCCACGGCAT | CGACCAGCAA | GTGTTGCCGA | 4320 |
| CGTATGCGGT | GATTTGCTGT | CCGGCGTTTG | GTGCGGCCGC | AAAGGTGGGA | ACATTCAACC | 4380 |
| CGGCGGCGCT | GCTACACGGC | TCCCAGGGCA | TCCGGCTGCA | TGCGCCGCTG | CCGGCGGCGG | 4440 |
| GAAAACTGTC | GGTGGTCACC | GAGGTCGCCG | ACATCCAGGA | CAAGGGGGAG | GGCAAGAACG | 4500 |
| CCATCGTTGT | GCTGCGCGGC | CGCGGTTGCG | ACCCGGAATC | GGGTTCGTTG | GTTGCCGAAA | 4560 |
| CGCTTACCAC | GTTGGTGCTT | CGGGGTCAGG | GGGGTTTCGG | AGGAGCGCGG | GGTGAGCGGC | 4620 |
| CGGCCGCGCC | GGAATTTCCG | GACCGCCACC | CCGACGCCCG | AATCGATATG | CCGACCCGTG | 4680 |
| AGGACCAGGC | GCTGATCTAC | CGGCTCTCCG | GTGACCGCAA | CCCGCTGCAC | AGCGACCCCT | 4740 |
| GGTTCGCCAC | GCAGCTGGCC | GGGTTTCCCA | AGCCGATCCT | GCACGGGTTG | TGCACCTACG | 4800 |
| GGGTGGCGGG | CCGGGCGCTG | GTGGCCGAGC | TTGGCGGCGG | TGTGGCGGCC | AACATCACCT | 4860 |
| CGATCGCCGC | GCGGTTCACC | AAGCCGGTGT | TTCCGGCGA | DACGCTGTCG | ACGGTGATCT | 4920 |
| GGCGCACCGA | GCCGGGCCGG | GCGGTGTTCC | GCACCGAGGT | GGCCGGCTCC | GACGGCGCCG | 4980 |
| AGGCCCGGGT | GGTGCTCGAC | GACGGCGCGG | TGGAGTACGT | GGCGGGTTAG | CTGCGCCGAG | 5040 |
| CGAGCGCAAA | ATCGCCCAAT | TCGGCACGAA | ATTGGGCGAT | TTTGCGTCTG | CTCGCGGGCC | 5100 |

( 2 ) INFORMATION FOR SEQ ID NO:2:

( i ) SEQUENCE CHARACTERISTICS:
        ( A ) LENGTH: 864 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium tuberculosis ( i x ) FEATURE:
        ( A ) NAME/KEY: CDS
        ( B ) LOCATION: 1..861
        ( D ) OTHER INFORMATION: /product="cma"

( x i ) SEQUENCE DESCRIPTION: SEQ ID NO:2:

| | | | | | | | | | | | | | | | | |
|---|---|---|---|---|---|---|---|---|---|---|---|---|---|---|---|---|
| ATG | CCC | GAC | GAG | CTG | AAG | CCG | CAC | TTC | GCC | AAC | GTG | CAG | GCG | CAC | TAC | 48 |
| Met | Pro | Asp | Glu | Leu | Lys | Pro | His | Phe | Ala | Asn | Val | Gln | Ala | His | Tyr | |
| 1 | | | | 5 | | | | | 10 | | | | | 15 | | |
| GAC | CTG | TCC | GAC | GAC | TTC | TTC | CGG | CTG | TTC | CTC | GAT | CCC | ACT | CAG | ACC | 96 |
| Asp | Leu | Ser | Asp | Asp | Phe | Phe | Arg | Leu | Phe | Leu | Asp | Pro | Thr | Gln | Thr | |
| | | | 20 | | | | | 25 | | | | | 30 | | | |
| TAC | AGC | TGC | GCC | TAC | TTC | GAG | CGC | GAC | GAC | ATG | ACG | CTG | CAA | GAG | GCG | 144 |
| Tyr | Ser | Cys | Ala | Tyr | Phe | Glu | Arg | Asp | Asp | Met | Thr | Leu | Gln | Glu | Ala | |
| | | 35 | | | | | 40 | | | | | 45 | | | | |
| CAG | ATC | GCC | AAG | ATC | GAT | CTC | GCG | CTG | GGC | AAA | CTC | GGA | TTG | CAG | CCG | 192 |
| Gln | Ile | Ala | Lys | Ile | Asp | Leu | Ala | Leu | Gly | Lys | Leu | Gly | Leu | Gln | Pro | |
| | | | 50 | | | | 55 | | | | | 60 | | | | |
| GGC | ATG | ACA | CTG | TTG | GAC | GTC | GGC | TGC | GGC | TGG | GGC | GCC | ACC | ATG | ATG | 240 |
| Gly | Met | Thr | Leu | Leu | Asp | Val | Gly | Cys | Gly | Trp | Gly | Ala | Thr | Met | Met | |
| 65 | | | | | 70 | | | | | 75 | | | | | 80 | |
| CGC | GCG | GTG | GAA | AAA | TAC | GAC | GTC | AAC | GTC | GTC | GGT | CTG | ACC | CTG | AGC | 288 |
| Arg | Ala | Val | Glu | Lys | Tyr | Asp | Val | Asn | Val | Val | Gly | Leu | Thr | Leu | Ser | |
| | | | | 85 | | | | | 90 | | | | | 95 | | |
| AAA | AAC | CAG | GCC | AAC | CAC | GTT | CAG | CAG | CTG | GTC | GCC | AAC | TCC | GAA | AAT | 336 |
| Lys | Asn | Gln | Ala | Asn | His | Val | Gln | Gln | Leu | Val | Ala | Asn | Ser | Glu | Asn | |
| | | | 100 | | | | 105 | | | | | 110 | | | | |
| CTA | CGC | TCC | AAA | CGC | GTT | CTG | CTG | GCC | GGC | TGG | GAA | CAG | TTT | GAC | GAG | 384 |
| Leu | Arg | Ser | Lys | Arg | Val | Leu | Leu | Ala | Gly | Trp | Glu | Gln | Phe | Asp | Glu | |
| | | 115 | | | | | 120 | | | | | 125 | | | | |
| CCC | GTC | GAC | CGC | ATC | GTC | AGC | ATC | GGT | GCT | TTC | GAA | CAT | TTC | GGT | CAC | 432 |
| Pro | Val | Asp | Arg | Ile | Val | Ser | Ile | Gly | Ala | Phe | Glu | His | Phe | Gly | His | |
| | 130 | | | | | 135 | | | | | 140 | | | | | |
| GAG | CGC | TAC | GAC | GCG | TTC | TTC | AGC | CTG | GCG | CAT | CGC | CTG | CTG | CCC | GCT | 480 |
| Glu | Arg | Tyr | Asp | Ala | Phe | Phe | Ser | Leu | Ala | His | Arg | Leu | Leu | Pro | Ala | |
| 145 | | | | | 150 | | | | | 155 | | | | | 160 | |
| GAC | GGG | GTC | ATG | CTG | CTG | CAC | ACC | ATC | ACC | GGG | TTG | CAT | CCG | AAA | GAG | 528 |
| Asp | Gly | Val | Met | Leu | Leu | His | Thr | Ile | Thr | Gly | Leu | His | Pro | Lys | Glu | |
| | | | | 165 | | | | | 170 | | | | | 175 | | |
| ATC | CAC | GAA | CGC | GGC | CTG | CCC | ATG | TCG | TTC | ACC | TTC | GCT | CGT | TTC | CTG | 576 |
| Ile | His | Glu | Arg | Gly | Leu | Pro | Met | Ser | Phe | Thr | Phe | Ala | Arg | Phe | Leu | |
| | | | 180 | | | | | 185 | | | | | 190 | | | |
| AAA | TTC | ATT | GTG | ACC | GAG | ATC | TTT | CCG | GGT | GGG | CGG | CTG | CCC | TCG | ATA | 624 |
| Lys | Phe | Ile | Val | Thr | Glu | Ile | Phe | Pro | Gly | Gly | Arg | Leu | Pro | Ser | Ile | |
| | | 195 | | | | | 200 | | | | | 205 | | | | |
| CCG | ATG | GTG | CAG | GAG | TGT | GCC | AGC | GCA | AAC | GGC | TTC | ACC | GTC | ACC | AGA | 672 |
| Pro | Met | Val | Gln | Glu | Cys | Ala | Ser | Ala | Asn | Gly | Phe | Thr | Val | Thr | Arg | |
| | 210 | | | | | 215 | | | | | 220 | | | | | |
| GTT | CAA | TCG | TTG | CAG | CCG | CAC | TAT | GCG | AAA | ACC | CTC | GAC | CTC | TGG | TCC | 720 |
| Val | Gln | Ser | Leu | Gln | Pro | His | Tyr | Ala | Lys | Thr | Leu | Asp | Leu | Trp | Ser | |
| 225 | | | | | 230 | | | | | 235 | | | | | 240 | |
| GCG | GCG | TTG | CAG | GCC | AAC | AAG | GGC | CAG | GCC | ATC | GCG | CTG | CAA | TCC | GAG | 768 |
| Ala | Ala | Leu | Gln | Ala | Asn | Lys | Gly | Gln | Ala | Ile | Ala | Leu | Gln | Ser | Glu | |
| | | | | 245 | | | | | 250 | | | | | 255 | | |
| GAA | GTC | TAC | GAG | CGG | TAT | ATG | AAG | TAC | CTC | ACC | GGC | TGC | GCC | GAG | ATG | 816 |
| Glu | Val | Tyr | Glu | Arg | Tyr | Met | Lys | Tyr | Leu | Thr | Gly | Cys | Ala | Glu | Met | |
| | | | 260 | | | | | 265 | | | | | 270 | | | |
| TTT | CGC | ATC | GGA | TAC | ATC | GAC | GTC | AAC | CAG | TTC | ACC | TGC | CAG | AAG | | 861 |
| Phe | Arg | Ile | Gly | Tyr | Ile | Asp | Val | Asn | Gln | Phe | Thr | Cys | Gln | Lys | | |
| | | 275 | | | | | 280 | | | | | 285 | | | | |
| TGA | | | | | | | | | | | | | | | | 864 |

( 2 ) INFORMATION FOR SEQ ID NO:3:

( i ) SEQUENCE CHARACTERISTICS:
        ( A ) LENGTH: 287 amino acids
        ( B ) TYPE: amino acid (D) TOPOLOGY: linear (ii) MOLECULE TYPE: MACE protein (xi) SEQUENCE DESCRIPTION: SEQ ID NO:3:

| Met | Pro | Asp | Glu | Leu | Lys | Pro | His | Phe | Ala | Asn | Val | Gln | Ala | His | Tyr |
|---|---|---|---|---|---|---|---|---|---|---|---|---|---|---|---|
| 1 | | | | 5 | | | | | 10 | | | | | 15 | |

| Asp | Leu | Ser | Asp | Asp | Phe | Phe | Arg | Leu | Phe | Leu | Asp | Pro | Thr | Gln | Thr |
|---|---|---|---|---|---|---|---|---|---|---|---|---|---|---|---|
| | | | 20 | | | | | 25 | | | | | 30 | | |

| Tyr | Ser | Cys | Ala | Tyr | Phe | Glu | Arg | Asp | Asp | Met | Thr | Leu | Gln | Glu | Ala |
|---|---|---|---|---|---|---|---|---|---|---|---|---|---|---|---|
| | | 35 | | | | | 40 | | | | | 45 | | | |

| Gln | Ile | Ala | Lys | Ile | Asp | Leu | Ala | Leu | Gly | Lys | Leu | Gly | Leu | Gln | Pro |
|---|---|---|---|---|---|---|---|---|---|---|---|---|---|---|---|
| | 50 | | | | | 55 | | | | | 60 | | | | |

| Gly | Met | Thr | Leu | Leu | Asp | Val | Gly | Cys | Gly | Trp | Gly | Ala | Thr | Met | Met |
|---|---|---|---|---|---|---|---|---|---|---|---|---|---|---|---|
| 65 | | | | | 70 | | | | | 75 | | | | | 80 |

| Arg | Ala | Val | Glu | Lys | Tyr | Asp | Val | Asn | Val | Gly | Leu | Thr | Leu | Ser |
|---|---|---|---|---|---|---|---|---|---|---|---|---|---|---|
| | | | | 85 | | | | | 90 | | | | | 95 |

| Lys | Asn | Gln | Ala | Asn | His | Val | Gln | Gln | Leu | Val | Ala | Asn | Ser | Glu | Asn |
|---|---|---|---|---|---|---|---|---|---|---|---|---|---|---|---|
| | | | 100 | | | | | 105 | | | | | 110 | | |

| Leu | Arg | Ser | Lys | Arg | Val | Leu | Leu | Ala | Gly | Trp | Glu | Gln | Phe | Asp | Glu |
|---|---|---|---|---|---|---|---|---|---|---|---|---|---|---|---|
| | | 115 | | | | | 120 | | | | | 125 | | | |

| Pro | Val | Asp | Arg | Ile | Val | Ser | Ile | Gly | Ala | Phe | Glu | His | Phe | Gly | His |
|---|---|---|---|---|---|---|---|---|---|---|---|---|---|---|---|
| | 130 | | | | | 135 | | | | | 140 | | | | |

| Glu | Arg | Tyr | Asp | Ala | Phe | Phe | Ser | Leu | Ala | His | Arg | Leu | Leu | Pro | Ala |
|---|---|---|---|---|---|---|---|---|---|---|---|---|---|---|---|
| 145 | | | | | 150 | | | | | 155 | | | | | 160 |

| Asp | Gly | Val | Met | Leu | Leu | His | Thr | Ile | Thr | Gly | Leu | His | Pro | Lys | Glu |
|---|---|---|---|---|---|---|---|---|---|---|---|---|---|---|---|
| | | | | 165 | | | | | 170 | | | | | 175 | |

| Ile | His | Glu | Arg | Gly | Leu | Pro | Met | Ser | Phe | Thr | Phe | Ala | Arg | Phe | Leu |
|---|---|---|---|---|---|---|---|---|---|---|---|---|---|---|---|
| | | | 180 | | | | | 185 | | | | | 190 | | |

| Lys | Phe | Ile | Val | Thr | Glu | Ile | Phe | Pro | Gly | Gly | Arg | Leu | Pro | Ser | Ile |
|---|---|---|---|---|---|---|---|---|---|---|---|---|---|---|---|
| | | 195 | | | | | 200 | | | | | 205 | | | |

| Pro | Met | Val | Gln | Glu | Cys | Ala | Ser | Ala | Asn | Gly | Phe | Thr | Val | Thr | Arg |
|---|---|---|---|---|---|---|---|---|---|---|---|---|---|---|---|
| | 210 | | | | | 215 | | | | | 220 | | | | |

| Val | Gln | Ser | Leu | Gln | Pro | His | Tyr | Ala | Lys | Thr | Leu | Asp | Leu | Trp | Ser |
|---|---|---|---|---|---|---|---|---|---|---|---|---|---|---|---|
| 225 | | | | | 230 | | | | | 235 | | | | | 240 |

| Ala | Ala | Leu | Gln | Ala | Asn | Lys | Gly | Gln | Ala | Ile | Ala | Leu | Gln | Ser | Glu |
|---|---|---|---|---|---|---|---|---|---|---|---|---|---|---|---|
| | | | | 245 | | | | | 250 | | | | | 255 | |

| Glu | Val | Tyr | Glu | Arg | Tyr | Met | Lys | Tyr | Leu | Thr | Gly | Cys | Ala | Glu | Met |
|---|---|---|---|---|---|---|---|---|---|---|---|---|---|---|---|
| | | | 260 | | | | | 265 | | | | | 270 | | |

| Phe | Arg | Ile | Gly | Tyr | Ile | Asp | Val | Asn | Gln | Phe | Thr | Cys | Gln | Lys |
|---|---|---|---|---|---|---|---|---|---|---|---|---|---|---|
| | | 275 | | | | | 280 | | | | | 285 | | |

(2) INFORMATION FOR SEQ ID NO:4:

(i) SEQUENCE CHARACTERISTICS:
      (A) LENGTH: 1155 base pairs
      (B) TYPE: nucleic acid
      (C) STRANDEDNESS: single
      (D) TOPOLOGY: linear (ii) MOLECULE TYPE: DNA (genomic)

(vi) ORIGINAL SOURCE:
      (A) ORGANISM: Mycobacterium tuberculosis (ix) FEATURE:
      (A) NAME/KEY: CDS
      (B) LOCATION: complement (4..1155)
      (D) OTHER INFORMATION: /product="ORF2"

(xi) SEQUENCE DESCRIPTION: SEQ ID NO:4:

-continued

```
CTACCAATGC  ACACCGGGCA  CCAGTCGCCC  CAAGCGCCTG  AGCGGCCTCG  GGACTCCCGC    60
GCGGGCGGAT  CGCCGGGGAC  GCCGCGGCGC  CGGTGGGCGG  TCCGCGTCTG  GACGCGAAAT   120
CCCCTGCGCT  GCAGCTGAAT  CGGGATAGCC  CAGATAGAGC  TGGTGCAGAA  TTCGGCGCGA   180
CAGCCGTGGC  GCGACGTAGT  TGCCGGCTTC  GGCGAGCGTA  CCCAACGGAG  TGTCGATGCG   240
CGCCGGCTTT  TCCACGAGTC  CGCGGATCAC  CATCGCCGCC  GCGCGTTCGC  GGCTGATCGC   300
GCGCACCGGG  TTGAGCCGCC  GCGACGGCAC  GATCATCGGG  GTGGCCACCA  GCGGCATATG   360
GATGTTGGTG  AACGTGATGT  GGTCGGACAG  CGTCTCGGAG  GCGACCACGT  CGGCGAACGC   420
GTCCAGCGCG  GCCTTGGTGG  GCAGATACGA  GCTGTACTTG  GGATTGCGGG  CCTGCACGCC   480
GGCGCTGGAG  ACGTTGACGA  CGTGGCCGAA  CCGGCGCTCG  CGCCAATGCG  GCAGCAGCGC   540
CAGCACCATG  CGCACCGCGC  CGAAGTAGTT  GACCGCCATC  ACCCGCTCGT  AGTCGTGCAG   600
CCGGTCGGTG  GAGTTGACCA  CCGAGCGGCG  TATCGACCGG  CCGGCGTTGT  TCACCAGGTA   660
GTCCACGTGG  TCGAAACGGC  CCAGGATGTC  CTTGACGGTG  TGCTCCACCG  ACGCGGAATC   720
GGTGACGTCG  CAGGTGAATG  CGTGCGCCTG  ACCGCCATGG  GCGCGGATCT  CGGTGACCAG   780
CTCATCTAGC  GCGTTGCCGT  TGCGGGCCAG  CGCGAATACC  GTCGCACCCC  GTTTGGCGAC   840
GGCGATCGCC  GATGCCCTCC  CGATGCCGCT  GGACGCACCG  GTGATGATGA  CGTGGCGGCC   900
CAGCAGCGGA  TCGTTGCGAC  GCGCGCGGTC  GGGGTCGAGG  TGCTCGGCCC  AATACCGCCA   960
CAGCCCGGGC  GCGTAGGTGG  CGAATTCGGG  GACGTGAATG  CCGGTGCCGC  GCAACGCTTC  1020
CCGGGTTGTG  TCGGACGTGA  ACGTGGGCGC  GCAGCCGACG  ACGTCGAAAA  TCTCGGCGGG  1080
AATTCCCAGT  TGGGTGGCCG  CCATGTTGCG  CAGCACCTTG  GCGCGGCCGC  GCGCGTTGAG  1140
CACCGGTGCG  GCCAC                                                       1155
```

( 2 ) INFORMATION FOR SEQ ID NO:5:

( i ) SEQUENCE CHARACTERISTICS:
    ( A ) LENGTH: 384 amino acids
    ( B ) TYPE: amino acid
    ( D ) TOPOLOGY: linear ( i i ) MOLECULE TYPE: ORF2 protein ( x i ) SEQUENCE DESCRIPTION: SEQ ID NO:5:

```
Val Ala Ala Pro Val Leu Asn Ala Arg Gly Arg Ala Lys Val Leu Arg
 1               5                  10                  15

Asn Met Ala Ala Thr Gln Leu Gly Ile Pro Ala Glu Ile Phe Asp Val
                20                  25                  30

Val Gly Cys Ala Pro Thr Phe Thr Ser Asp Thr Thr Arg Glu Ala Leu
            35                  40                  45

Arg Gly Thr Gly Ile His Val Pro Glu Phe Ala Thr Tyr Ala Pro Gly
        50                  55                  60

Leu Trp Arg Tyr Trp Ala Glu His Leu Asp Pro Asp Arg Ala Arg Arg
65                  70                  75                  80

Asn Asp Pro Leu Leu Gly Arg His Val Ile Ile Thr Gly Ala Ser Ser
                85                  90                  95

Gly Ile Gly Arg Ala Ser Ala Ile Ala Val Ala Lys Arg Gly Ala Thr
            100                 105                 110

Val Phe Ala Leu Ala Arg Asn Gly Asn Ala Leu Asp Glu Leu Val Thr
        115                 120                 125

Glu Ile Arg Ala His Gly Gly Gln Ala His Ala Phe Thr Cys Asp Val
    130                 135                 140
```

| Thr | Asp | Ser | Ala | Ser | Val | Glu | His | Thr | Val | Lys | Asp | Ile | Leu | Gly | Arg |
| 145 | | | | 150 | | | | | 155 | | | | | | 160 |

| Phe | Asp | His | Val | Asp | Tyr | Leu | Val | Asn | Asn | Ala | Gly | Arg | Ser | Ile | Arg |
| | | | 165 | | | | | 170 | | | | | 175 | | |

| Arg | Ser | Val | Val | Asn | Ser | Thr | Asp | Arg | Leu | His | Asp | Tyr | Glu | Arg | Val |
| | | | 180 | | | | | 185 | | | | | 190 | | |

| Met | Ala | Val | Asn | Tyr | Phe | Gly | Ala | Val | Arg | Met | Val | Leu | Ala | Leu | Leu |
| | | 195 | | | | | 200 | | | | | 205 | | | |

| Pro | His | Trp | Arg | Glu | Arg | Arg | Phe | Gly | His | Val | Val | Asn | Val | Ser | Ser |
| | 210 | | | | | 215 | | | | | 220 | | | | |

| Ala | Gly | Val | Gln | Ala | Arg | Asn | Pro | Lys | Tyr | Ser | Ser | Tyr | Leu | Pro | Thr |
| 225 | | | | | 230 | | | | | 235 | | | | | 240 |

| Lys | Ala | Ala | Leu | Asp | Ala | Phe | Ala | Asp | Val | Val | Ala | Ser | Glu | Thr | Leu |
| | | | | 245 | | | | | 250 | | | | | 255 | |

| Ser | Asp | His | Ile | Thr | Phe | Thr | Asn | Ile | His | Met | Pro | Leu | Val | Ala | Thr |
| | | | 260 | | | | | 265 | | | | | 270 | | |

| Pro | Met | Ile | Val | Pro | Ser | Arg | Arg | Leu | Asn | Pro | Val | Arg | Ala | Ile | Ser |
| | | 275 | | | | | 280 | | | | | 285 | | | |

| Arg | Glu | Arg | Ala | Ala | Ala | Met | Val | Ile | Arg | Gly | Leu | Val | Glu | Lys | Pro |
| | 290 | | | | | 295 | | | | | 300 | | | | |

| Ala | Arg | Ile | Asp | Thr | Pro | Leu | Gly | Thr | Leu | Ala | Glu | Ala | Gly | Asn | Tyr |
| 305 | | | | | 310 | | | | | 315 | | | | | 320 |

| Val | Ala | Pro | Arg | Leu | Ser | Arg | Arg | Ile | Leu | His | Gln | Leu | Tyr | Leu | Gly |
| | | | | 325 | | | | | 330 | | | | | 335 | |

| Tyr | Pro | Asp | Ser | Ala | Ala | Ala | Gln | Gly | Ile | Ser | Arg | Pro | Asp | Ala | Asp |
| | | | 340 | | | | | 345 | | | | | 350 | | |

| Arg | Pro | Pro | Ala | Pro | Arg | Arg | Pro | Arg | Arg | Ser | Ala | Arg | Ala | Gly | Val |
| | | 355 | | | | | 360 | | | | | 365 | | | |

| Pro | Arg | Pro | Leu | Arg | Arg | Leu | Gly | Arg | Leu | Val | Pro | Gly | Val | His | Trp |
| | 370 | | | | | 375 | | | | | 380 | | | | |

( 2 ) INFORMATION FOR SEQ ID NO:6:

( i ) SEQUENCE CHARACTERISTICS:
        ( A ) LENGTH: 873 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium tuberculosis ( i x ) FEATURE:
        ( A ) NAME/KEY: CDS
        ( B ) LOCATION: 1..870
        ( D ) OTHER INFORMATION: /product="ORF3"

( x i ) SEQUENCE DESCRIPTION: SEQ ID NO:6:

| ATG | GCG | ATT | GAT | CCG | AAC | TCC | ATA | GGT | GCA | GTG | ACC | GAG | CCG | ATG | TTG | 48 |
| Met | Ala | Ile | Asp | Pro | Asn | Ser | Ile | Gly | Ala | Val | Thr | Glu | Pro | Met | Leu | |
| 385 | | | | | 390 | | | | | 395 | | | | | 400 | |

| TTC | GAG | TGG | ACC | GAC | CGG | GAC | ACG | CTG | CTT | TAC | GCG | ATC | GGG | GTG | GGC | 96 |
| Phe | Glu | Trp | Thr | Asp | Arg | Asp | Thr | Leu | Leu | Tyr | Ala | Ile | Gly | Val | Gly | |
| | | | | 405 | | | | | 410 | | | | | 415 | | |

| GCC | GGG | ACC | GGA | GAT | CTG | GCG | TTC | ACC | ACG | GAG | AAC | AGC | CAC | GGC | ATC | 144 |
| Ala | Gly | Thr | Gly | Asp | Leu | Ala | Phe | Thr | Thr | Glu | Asn | Ser | His | Gly | Ile | |
| | | | 420 | | | | | 425 | | | | | 430 | | | |

| GAC | CAG | CAA | GTG | TTG | CCG | ACG | TAT | GCG | GTG | ATT | TGC | TGT | CCG | GCG | TTT | 192 |
| Asp | Gln | Gln | Val | Leu | Pro | Thr | Tyr | Ala | Val | Ile | Cys | Cys | Pro | Ala | Phe | |

|     |     |     |     | 435 |     |     |     |     | 440 |     |     |     |     | 445 |     |     |
|-----|-----|-----|-----|-----|-----|-----|-----|-----|-----|-----|-----|-----|-----|-----|-----|-----|
| GGT | GCG | GCC | GCA | AAG | GTG | GGA | ACA | TTC | AAC | CCG | GCG | GCG | CTG | CTA | CAC | 240 |
| Gly | Ala | Ala | Ala | Lys | Val | Gly | Thr | Phe | Asn | Pro | Ala | Ala | Leu | Leu | His |     |
|     | 450 |     |     |     |     | 455 |     |     |     |     | 460 |     |     |     |     |     |

```
GGC TCC CAG GGC ATC CGG CTG CAT GCG CCG CTG CCG GCG GCG GGA AAA    288
Gly Ser Gln Gly Ile Arg Leu His Ala Pro Leu Pro Ala Ala Gly Lys
465             470             475             480

CTG TCG GTG GTC ACC GAG GTC GCC GAC ATC CAG GAC AAG GGG GAG GGC    336
Leu Ser Val Val Thr Glu Val Ala Asp Ile Gln Asp Lys Gly Glu Gly
            485             490             495

AAG AAC GCC ATC GTT GTG CTG CGC GGC CGC GGT TGC GAC CCG GAA TCG    384
Lys Asn Ala Ile Val Val Leu Arg Gly Arg Gly Cys Asp Pro Glu Ser
        500             505             510

GGT TCG TTG GTT GCC GAA ACG CTT ACC ACG TTG GTG CTT CGG GGT CAG    432
Gly Ser Leu Val Ala Glu Thr Leu Thr Thr Leu Val Leu Arg Gly Gln
        515             520             525

GGG GGT TTC GGA GGA GCG CGG GGT GAG CGG CCG GCC GCG CCG GAA TTT    480
Gly Gly Phe Gly Gly Ala Arg Gly Glu Arg Pro Ala Ala Pro Glu Phe
    530             535             540

CCG GAC CGC CAC CCC GAC GCC CGA ATC GAT ATG CCG ACC CGT GAG GAC    528
Pro Asp Arg His Pro Asp Ala Arg Ile Asp Met Pro Thr Arg Glu Asp
545             550             555             560

CAG GCG CTG ATC TAC CGG CTC TCC GGT GAC CGC AAC CCG CTG CAC AGC    576
Gln Ala Leu Ile Tyr Arg Leu Ser Gly Asp Arg Asn Pro Leu His Ser
            565             570             575

GAC CCC TGG TTC GCC ACG CAG CTG GCC GGG TTT CCC AAG CCG ATC CTG    624
Asp Pro Trp Phe Ala Thr Gln Leu Ala Gly Phe Pro Lys Pro Ile Leu
            580             585             590

CAC GGG TTG TGC ACC TAC GGG GTG GCG GGC CGG GCG CTG GTG GCC GAG    672
His Gly Leu Cys Thr Tyr Gly Val Ala Gly Arg Ala Leu Val Ala Glu
        595             600             605

CTT GGC GGC GGT GTG GCG GCC AAC ATC ACC TCG ATC GCC GCG CGG TTC    720
Leu Gly Gly Gly Val Ala Ala Asn Ile Thr Ser Ile Ala Ala Arg Phe
    610             615             620

ACC AAG CCG GTG TTT CCC GGC GAG ACG CTG TCG ACG GTG ATC TGG CGC    768
Thr Lys Pro Val Phe Pro Gly Glu Thr Leu Ser Thr Val Ile Trp Arg
625             630             635             640

ACC GAG CCG GGC CGG GCG GTG TTC CGC ACC GAG GTG GCC GGC TCC GAC    816
Thr Glu Pro Gly Arg Ala Val Phe Arg Thr Glu Val Ala Gly Ser Asp
            645             650             655

GGC GCC GAG GCC CGG GTG GTG CTC GAC GAC GGC GCG GTG GAG TAC GTG    864
Gly Ala Glu Ala Arg Val Val Leu Asp Asp Gly Ala Val Glu Tyr Val
        660             665             670

GCG GGT TAG                                                        873
Ala Gly
```

( 2 ) INFORMATION FOR SEQ ID NO:7:

( i ) SEQUENCE CHARACTERISTICS:
( A ) LENGTH: 290 amino acids
( B ) TYPE: amino acid
( D ) TOPOLOGY: linear ( i i ) MOLECULE TYPE: ORF3 protein ( x i ) SEQUENCE DESCRIPTION: SEQ ID NO:7:

```
Met Ala Ile Asp Pro Asn Ser Ile Gly Ala Val Thr Glu Pro Met Leu
 1               5                  10                  15

Phe Glu Trp Thr Asp Arg Asp Thr Leu Leu Tyr Ala Ile Gly Val Gly
                20                  25                  30

Ala Gly Thr Gly Asp Leu Ala Phe Thr Thr Glu Asn Ser His Gly Ile
```

|       |       |       |       | 35    |       |       |       |       | 40    |       |       |       |       | 45    |       |
|-------|-------|-------|-------|-------|-------|-------|-------|-------|-------|-------|-------|-------|-------|-------|-------|

Asp Gln Gln Val Leu Pro Thr Tyr Ala Val Ile Cys Cys Pro Ala Phe
      50                     55                     60

Gly Ala Ala Ala Lys Val Gly Thr Phe Asn Pro Ala Ala Leu Leu His
65                 70                  75                    80

Gly Ser Gln Gly Ile Arg Leu His Ala Pro Leu Pro Ala Ala Gly Lys
                  85                  90                    95

Leu Ser Val Val Thr Glu Val Ala Asp Ile Gln Asp Lys Gly Glu Gly
           100                  105                 110

Lys Asn Ala Ile Val Val Leu Arg Gly Arg Gly Cys Asp Pro Glu Ser
        115                  120                125

Gly Ser Leu Val Ala Glu Thr Leu Thr Thr Leu Val Leu Arg Gly Gln
    130                    135                 140

Gly Gly Phe Gly Gly Ala Arg Gly Glu Arg Pro Ala Ala Pro Glu Phe
145                150                 155               160

Pro Asp Arg His Pro Asp Ala Arg Ile Asp Met Pro Thr Arg Glu Asp
               165                  170              175

Gln Ala Leu Ile Tyr Arg Leu Ser Gly Asp Arg Asn Pro Leu His Ser
         180                 185                190

Asp Pro Trp Phe Ala Thr Gln Leu Ala Gly Phe Pro Lys Pro Ile Leu
      195                 200                205

His Gly Leu Cys Thr Tyr Gly Val Ala Gly Arg Ala Leu Val Ala Glu
210                     215                220

Leu Gly Gly Gly Val Ala Ala Asn Ile Thr Ser Ile Ala Ala Arg Phe
225                230               235              240

Thr Lys Pro Val Phe Pro Gly Glu Thr Leu Ser Thr Val Ile Trp Arg
               245                 250              255

Thr Glu Pro Gly Arg Ala Val Phe Arg Thr Glu Val Ala Gly Ser Asp
        260                265               270

Gly Ala Glu Ala Arg Val Val Leu Asp Asp Gly Ala Val Glu Tyr Val
    275                  280                285

Ala Gly
290

(2) INFORMATION FOR SEQ ID NO:8:

(i) SEQUENCE CHARACTERISTICS:
        (A) LENGTH: 308 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (A) ORGANISM: Mycobacterium leprae (xi) SEQUENCE DESCRIPTION: SEQ ID NO:8:

Met Val Pro Ser Gln Ser His Pro Ala Lys Thr Pro Arg Lys Gln Leu
1                 5                    10                15

Lys Pro Pro Ile Glu Ala Val Gln Ser His Tyr Asp Arg Ser Asn Glu
           20                  25                30

Phe Phe Lys Leu Trp Leu Asp Pro Ser Met Thr Tyr Ser Cys Ala Tyr
              35                 40                45

Phe Glu Arg Pro Asp Leu Thr Leu Glu Glu Ala Gln Arg Ala Lys Arg
        50                55                60

Asp Leu Ala Leu Ser Lys Leu Gly Leu Glu Pro Gly Met Thr Leu Leu
65                 70                  75                  80

```
Asp  Ile  Gly  Cys  Gly  Trp  Gly  Ser  Thr  Met  Leu  His  Ala  Ile  Glu  Lys
               85                      90                      95

Tyr  Asp  Val  Asn  Val  Ile  Gly  Leu  Thr  Leu  Ser  Ala  Asn  Gln  Leu  Ala
              100                     105                    110

His  Asn  Lys  Leu  Lys  Phe  Ala  Glu  Ile  Asp  His  Thr  Arg  Thr  Asp  Arg
              115                     120                    125

Thr  Lys  Asp  Val  Arg  Leu  Gln  Gly  Trp  Glu  Gln  Phe  Asp  Glu  Pro  Val
     130                     135                    140

Asp  Arg  Ile  Ile  Ser  Leu  Gly  Ala  Phe  Glu  His  Phe  Ala  Asp  Gly  Ala
145                          150                    155                    160

Gly  Asp  Ala  Gly  Phe  Glu  Arg  Tyr  Asp  Ser  Phe  Phe  Lys  Met  Cys  Tyr
                   165                     170                         175

Asp  Val  Leu  Pro  Asp  Asp  Gly  Arg  Met  Leu  Leu  His  Thr  Ile  Ile  Val
              180                     185                         190

Pro  Asp  Ala  Lys  Glu  Thr  Lys  Glu  Leu  Gly  Leu  Thr  Thr  Pro  Met  Ser
          195                     200                    205

Leu  Leu  Arg  Phe  Ile  Lys  Phe  Ile  Leu  Thr  Glu  Ile  Phe  Pro  Gly  Gly
     210                     215                    220

Arg  Leu  Pro  Lys  Ile  Ser  Gln  Val  Asp  His  Tyr  Ser  Ser  Asn  Ala  Gly
225                          230                    235                    240

Phe  Thr  Val  Glu  Arg  Tyr  His  Arg  Ile  Gly  Ser  His  Tyr  Val  Pro  Thr
                   245                     250                         255

Leu  Asn  Ala  Trp  Ala  Ala  Ala  Leu  Glu  Ala  His  Lys  Asp  Glu  Ala  Ile
               260                     265                    270

Ala  Leu  Gln  Gly  Arg  Gln  Ile  Tyr  Asp  Thr  Tyr  Met  His  Tyr  Leu  Thr
          275                     280                    285

Gly  Cys  Ser  Asp  Leu  Phe  Arg  Asp  Arg  Tyr  Thr  Asp  Val  Cys  Gln  Phe
     290                     295                    300

Thr  Leu  Val  Lys
305
```

(2) INFORMATION FOR SEQ ID NO:9:

(i) SEQUENCE CHARACTERISTICS:
        (A) LENGTH: 282 amino acids
        (B) TYPE: amino acid
        (C) STRANDEDNESS: Not Relevant
        (D) TOPOLOGY: Not Relevant (ii) MOLECULE TYPE: protein (vi) ORIGINAL SOURCE:
        (A) ORGANISM: Escherichia coli (xi) SEQUENCE DESCRIPTION: SEQ ID NO:9:

```
Ala  Arg  Leu  Phe  Asn  Leu  Gln  Ser  Lys  Lys  Arg  Ala  Trp  Ile  Val  Gly
1                   5                    10                         15

Lys  Glu  His  Tyr  Asp  Leu  Gly  Asn  Asp  Leu  Phe  Ser  Arg  Met  Leu  Asp
               20                     25                     30

Pro  Phe  Met  Gln  Tyr  Ser  Cys  Ala  Tyr  Trp  Lys  Asp  Ala  Asp  Asn  Leu
          35                     40                     45

Glu  Ser  Ala  Gln  Gln  Ala  Lys  Leu  Lys  Met  Ile  Cys  Glu  Lys  Leu  Gln
     50                     55                     60

Leu  Lys  Pro  Gly  Met  Arg  Val  Leu  Asp  Ile  Gly  Cys  Gly  Trp  Gly  Gly
65                       70                     75                         80

Leu  Ala  His  Tyr  Met  Ala  Ser  Asn  Tyr  Asp  Val  Ser  Val  Val  Gly  Val
               85                     90                         95
```

|     |     |     |     |     |     |     |     |     |     |     |     |     |     |     |
| --- | --- | --- | --- | --- | --- | --- | --- | --- | --- | --- | --- | --- | --- | --- |
| Thr | Ile | Ser | Ala 100 | Glu | Gln | Gln | Lys | Met 105 | Ala | Gln | Glu | Arg | Cys 110 | Glu | Gly |
| Leu | Asp | Val 115 | Thr | Ile | Leu | Leu | Gln 120 | Asp | Tyr | Arg | Asp | Leu 125 | Asn | Asp | Gln |
| Phe | Asp 130 | Arg | Ile | Val | Ser | Val 135 | Gly | Met | Phe | Glu | His 140 | Val | Gly | Pro | Lys |
| Asn 145 | Tyr | Asp | Thr | Tyr | Phe 150 | Ala | Val | Val | Asp | Arg 155 | Asn | Leu | Lys | Pro | Glu 160 |
| Gly | Ile | Phe | Leu | Leu 165 | His | Thr | Ile | Gly | Ser 170 | Lys | Lys | Thr | Asp 175 | Leu | Asn |
| Val | Asp | Pro | Trp 180 | Ile | Asn | Lys | Tyr | Ile 185 | Phe | Pro | Asn | Gly | Cys 190 | Leu | Pro |
| Ser | Val | Arg 195 | Gln | Ile | Ala | Gln | Ser 200 | Ser | Glu | Pro | His | Phe 205 | Val | Met | Glu |
| Asp | Trp 210 | His | Asn | Phe | Gly | Ala 215 | Asp | Tyr | Asp | Thr | Thr 220 | Leu | Met | Ala | Trp |
| Tyr 225 | Glu | Arg | Phe | Leu | Ala 230 | Ala | Trp | Pro | Glu | Ile 235 | Ala | Asp | Asn | Tyr | Ser 240 |
| Glu | Arg | Phe | Lys | Arg 245 | Met | Phe | Thr | Tyr | Leu 250 | Asn | Ala | Cys | Ala 255 | Gly |
| Ala | Phe | Arg | Ala 260 | Arg | Asp | Ile | Gln | Leu 265 | Trp | Gln | Val | Val | Phe 270 | Ser | Arg |
| Gly | Val | Glu 275 | Asn | Gly | Leu | Arg | Val 280 | Ala | Arg |

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Primer for cma"

( x i ) SEQUENCE DESCRIPTION: SEQ ID NO:10:

ATGCCCGACG AGCTGAAGCC GCACT        25

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Primer for cma"

( x i ) SEQUENCE DESCRIPTION: SEQ ID NO:11:

TCACTTCTGG CAGGTGAACT GGTTG        25

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Primer for Orf2."

( x i ) SEQUENCE DESCRIPTION: SEQ ID NO:12:

ATGGACACGA TCGACGGACC CTACT　　　　　　　　　　　　　　　　　　　　　　　　　　　25

( 2 ) INFORMATION FOR SEQ ID NO:13:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Primer for Orf3."

( x i ) SEQUENCE DESCRIPTION: SEQ ID NO:13:

TCACCTGCCA GAAGTGACTA CCAAT　　　　　　　　　　　　　　　　　　　　　　　　　　　25

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Primer for Orf3."

( x i ) SEQUENCE DESCRIPTION: SEQ ID NO:14:

ATGGCGATTG ATCCGAACTC CATAG　　　　　　　　　　　　　　　　　　　　　　　　　　　25

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Primer for Orf3."

( x i ) SEQUENCE DESCRIPTION: SEQ ID NO:15:

CTAACCCGCC ACGTACTCCA CCGCG　　　　　　　　　　　　　　　　　　　　　　　　　　　25

( 2 ) INFORMATION FOR SEQ ID NO:16:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Example 2 Primer"

( x i ) SEQUENCE DESCRIPTION: SEQ ID NO:16:

GCCATATGCT TCTTGCACTC GGCATAG　　　　　　　　　　　　　　　　　　　　　　　　　　27

( 2 ) INFORMATION FOR SEQ ID NO:17:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Example 2 Primer"

( x i ) SEQUENCE DESCRIPTION: SEQ ID NO:17:

CCATATGCAT TGCGAAGTGA TTCCTCC                                                                                    27

( 2 ) INFORMATION FOR SEQ ID NO:18:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Example 2 Primer"

( x i ) SEQUENCE DESCRIPTION: SEQ ID NO:18:

GGTCTAGAGC TTCTTGCACT CGGCATAGGC G                                                                               31

( 2 ) INFORMATION FOR SEQ ID NO:19:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Example 2 Primer"

( x i ) SEQUENCE DESCRIPTION: SEQ ID NO:19:

CCATATGCAT TGCGAAGTGA TTCCTCC                                                                                    27

( 2 ) INFORMATION FOR SEQ ID NO:20:

( i ) SEQUENCE CHARACTERISTICS:
        ( A ) LENGTH: 466 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Example 2 Modified promoter region."

( i x ) FEATURE:
        ( A ) NAME/KEY: CDS
        ( B ) LOCATION: 262..406

( x i ) SEQUENCE DESCRIPTION: SEQ ID NO:20:

```
ACTAGTCTAT AGGGAGACCA CAACGGTTTC CCTCTAGAGC TTCTTGCACT CGGCATAGGC        60

GAGTGCTAAG AATAACGTTG GCACTCGCGA CCGGTGAGTG CTAGGTCGGG ACGGTGAGGC       120

CAGGCCCGTC GTCGCAGCGA GTGGCAGCGA GGACAACTTG AGCCGTCCGT CGCGGGCACT       180

GCGCCCGGCC AGCGTAAGTA GCGGGGTTGC CGTCACCCGG TGACCCCGT TTCATCCCCG        240

ATCCGGAGGA ATCACTTCGC A ATG CAT ATG CGG GGT TCT CAT CAT CAT CAT        291
                         Met His Met Arg Gly Ser His His His His
                                             295             300

CAT CAT GGT ATG GCT AGC ATG ACT GGT GGA CAG CAA ATG GGT CGG GAT        339
His His Gly Met Ala Ser Met Thr Gly Gly Gln Gln Met Gly Arg Asp
            305                 310                 315

CTG TAC GAC GAT GAC GAT AAG GAT CCG AGC TCG AGA TCT GCA GCT GGT        387
Leu Tyr Asp Asp Asp Asp Lys Asp Pro Ser Ser Arg Ser Ala Ala Gly
            320                 325                 330

ACC ATG GAA TTC CAA GCT T GATCCGGCTG CTAACAAAGC CCGAAAGGAA             436
Thr Met Glu Phe Gln Ala
            335

GCTGAGTTGG CTGCTGCCAC CGCTACTAGT                                        466
```

( 2 ) INFORMATION FOR SEQ ID NO:21:

( i ) SEQUENCE CHARACTERISTICS:
        ( A ) LENGTH: 48 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Met His Met Arg Gly Ser His His His His His His Gly Met Ala Ser
 1               5                  10                  15

Met Thr Gly Gly Gln Gln Met Gly Arg Asp Leu Tyr Asp Asp Asp Asp
            20                  25                  30

Lys Asp Pro Ser Ser Arg Ser Ala Ala Gly Thr Met Glu Phe Gln Ala
            35              40                  45
```

DETERMINING THE ABILITY OF A COMPOUND TO INHIBIT THE CYCLOPROPANATION OF MYCOLIC ACIDS IN PATHOGENIC MYCOBACTERIA

TECHNICAL FIELD OF THE INVENTION

The present invention relates to DNA and protein compositions useful both for diagnosis and the design of therapeutics for treatment of tuberculosis and other mycobacterial infections. More specifically, the present invention relates to DNA and protein compositions which are responsible for the cyclopropanation of mycolic acids in *Mycobacterium tuberculosis* and other pathogenic forms of mycobacteria.

BACKGROUND OF THE INVENTION

Tuberculosis or "TB" is an acute or chronic infection caused by *Mycobacterium tuberculosis*. Tuberculosis continues to be a major health concern in both the United States and abroad. According to the World Health Organization's estimates, 1.7 billion people (one-third of the world population) harbor tuberculosis bacteria in their bodies and approximately 3 million of these people die each year from tuberculosis infection. See, Kaufman, et al., *Trends in Microbiology* 1:2–5 (1993). This means that tuberculosis is responsible for 6% of the total global mortality. See, Kaufman, id.

*Mycobacterium tuberculosis* is a member of the genus mycobacterium. Pathogenic Mycobacteria are mostly slow growing organisms which are shaped like straight or slightly curved rods and are sometimes branching or filamentous. Mycobacteria are sometimes referred to as acid-fast bacilli (AFB) because application of alcohol (e.g., acid-alcohol or 95% ethanol with 3% hydrochloric acid) to mycobacteria stained with basic dye will not decolorize them. Typically, mycobacteria are obligate aerobes and can be characterized as gram-positive.

Mycolic acids are major constituents of the mycobacterial cell wall, representing up to 30% of the dried cell mass. They are $\alpha$-alkyl, $\beta$-hydroxy fatty acids which in mycobacteria range in size from sixty to ninety carbons. Takayama and Qureshi, *The Mycobacteria: A Sourcebook*, Part A, G.P. Kubica and L.G. Wayne, Eds., Marcel Dekker, Inc., New York, N.Y. (1984). Since their isolation by Stodola, Lesuk and Anderson in 1938, the chemistry and structure of these lipids has become the subject of an extensive literature. See, Goren, *Bacteriol Rev.* 36, 33 (1972); Minnikin, *The Biology of the Mycobacteria*, C. Ratledge, and J. Stanford, Eds. (Academic Press, San Diego, Calif., 1982), pp. 95–184.

The genus mycobacterium includes a number of highly pathogenic organisms besides *M. tuberculosis*. These other pathogenic forms of mycobacteria include: *M. leprae, M. avium, M. bovis, M. chelonei* (also known as borstelense and abscessus), *M. africanum, M. marinium* (also known as balnei and platypoecilus, the causative agent of "swimming pool granuloma"), *M. buruli* (also known as ulcerans), *M. fortuitum* (also known as giae, minetti, and ranae), *M. haemophilum, M. intracellulare, M. kansasii* (also known as luciflavum), *M. littorale* (also known as xenopi), *M. malrnoense, M. marianum (also known as scrofulaceum and paraffinicum), M. simiae, M. szulgai,* and *M. ulcerans* (which is the agent responsible for Buruli ulcer). There are also non-pathogenic forms of mycobacteria which include: *M. gordonae* (also known as aquae), *M. gastri, M. phlei* (also known as moelleri and as timothy bacillus), *M. nonchromogenicum, M. smegmatis, M. terrae, M. triviale,* and *M. vaccae*.

It has been found that pathogenic and non-pathogenic forms of mycobacteria biosynthesize different mycolic acids. Pathogenic forms of mycobacteria, including *M. tuberculosis, M. avium, M. kansasi, M. leprae, M. ulcerans,* and *M. marinum*, uniformly modify their major mycolic acids at two positions by enzymatically transforming a double bond into a cyclopropane ring. Minnikin, *The Biology of the Mycobacteria*, C. Ratledge, and J. Stanford, Eds. (Academic Press, San Diego, Calif., 1982) pp. 95–184; Daffe et al., *Res. Microbiol* 142, 397(1991). By contrast, non-pathogenic mycobacteria, such as *M. smegmatis*, do not cyclopropanate their mycolic acids. This difference is illustrated in the proposed mycolic acid biosynthesis shown in FIG. 1 for the pathogenic mycobacterium *M. tuberculosis* and the non-pathogenic mycobacterium *M. smegmatis*.

Conventional therapy for tuberculosis includes treatment with such pharmaceuticals as isoniazid ("INH"), ethambutol, streptomycin, rifampin, rifabutin, clarithromycin, ciprofloxacin, clofazamine, azithromycin, ethionamide, pyrazinamide, amikacin and/or resorcinomycin A. A new therapeutic for tuberculosis is described in the inventors' co-pending application Ser. No. 08/210,519, the disclosures of which are incorporated by reference. In many cases, the initial treatment for tuberculosis includes INH in combination with at least one other drug, such as ethambutol, streptomycin, rifampin or ethionamide. While treatment of tuberculosis patients with drug therapies involving INH is often effective, use of INH can have serious drawbacks. For example, treatment with INH often causes severe, sometimes fatal, hepatitis. Also, INH causes peripheral neuropathy and liver dysfunction in some recipients. Moreover, there are emerging strains of *Mycobacterium tuberculosis* which are resistant to multiple existing drug treatments, particularly INH. See, D.E. Snider and W.L. Roper, *N. Engl. J. Med.* 326, 703 (1992). These new mutant strains of *Mycobacterium tuberculosis* will present grave public health risks in the years ahead unless new and more effective treatments are devised to combat them.

A large proportion of the current arsenal of chemotherapeutics against *Mycobacterium tuberculosis* and other pathogenic forms of mycobacteria are thought to affect the biosynthesis of the cell-wall components of such mycobacteria, particularly the mycolic acids. This biosynthetic pathway is thought to be the target of INH, ethionamide, thiocarlide and possibly ethambutol. See, A. Banerjee et al., *Science*, 263:227 (1994); F. Winder, *The Biology of The Mycobacteria*, Vol. 1, C. Rutledge, J. Stanford, Eds., Academic Press, San Diego, Calif. (1982). In spite of the importance of this biosynthetic pathway as a chemotherapeutic target, the inventors do not know of a single enzyme activity or gene directly involved in the biosynthesis of mycolic acids which has previously been identified in the art. Even the recent identification of the inhA gene by Banerjee et al. appears to relate to mycolate transport or an early component of fatty acid biosynthesis rather than a specific component of the mycolate biosynthetic pathway. A. Banerjee et al., id.

What is greatly needed in the art is the identification, isolation and purification of genes and enzymes involved in the biosynthesis of mycolic acids in pathogenic mycobacteria, particularly those genes and enzymes likely to be found in the new drug resistant strains of *Mycobacterium tuberculosis*. From such identification, isolation and purification, new therapeutics can be developed and tested. To the extent such genes and enzymes are common to all forms of

SUMMARY OF THE INVENTION

The gene and enzyme responsible for cyclopropanating mycolic acids in *M. tuberculosis* have been isolated and identified by the inventors. Since cyclopropanation of mycolic acids distinguishes pathogenic forms of mycobacterium from non-pathogenic forms, the present invention has importance for all pathogenic forms of mycobacterium, including the new mutant strains of *Mycobacterium tuberculosis*. More specifically, the present invention provides for: (1) recombinantly producing the enzyme responsible for cyclopropanation of mycolic acids in *M. tuberculosis*, namely Mycolic Acid Cyclopropanating Enzyme or "MACE" (SEQ. ID No. 3), (2) isolating the nucleic acid sequence which encodes MACE, namely cyclopropane mycolic acid synthase or "cma" (SEQ. ID No. 2), (3) providing other isolated nucleic acid and predicted amino acid sequences from *M. tuberculosis* (SEQ. ID Nos. 4, 5, 6 and 7), (4) using portions of the nucleic acid sequences of the present invention as probes to detect the presence of *M. tuberculosis*, (5) using MACE in an assay to test for the inhibition of enzymatic activity by prospective therapeutics, (6) producing antibodies which are specifically immunoreactive with MACE and (7) use of such antibodies in an immunoassay to detect the presence of the MACE protein.

BRIEF DESCRIPTION OF THE FIGURES

FIG. 2 shows the homology between MACE (SEQ. ID No. 3) and amino acid sequences for *M. leprae* and *E. coli* (SEQ ID Nos. 8,9).

DESCRIPTION OF THE SPECIFIC EMBODIMENTS

Definitions

Figure 1:
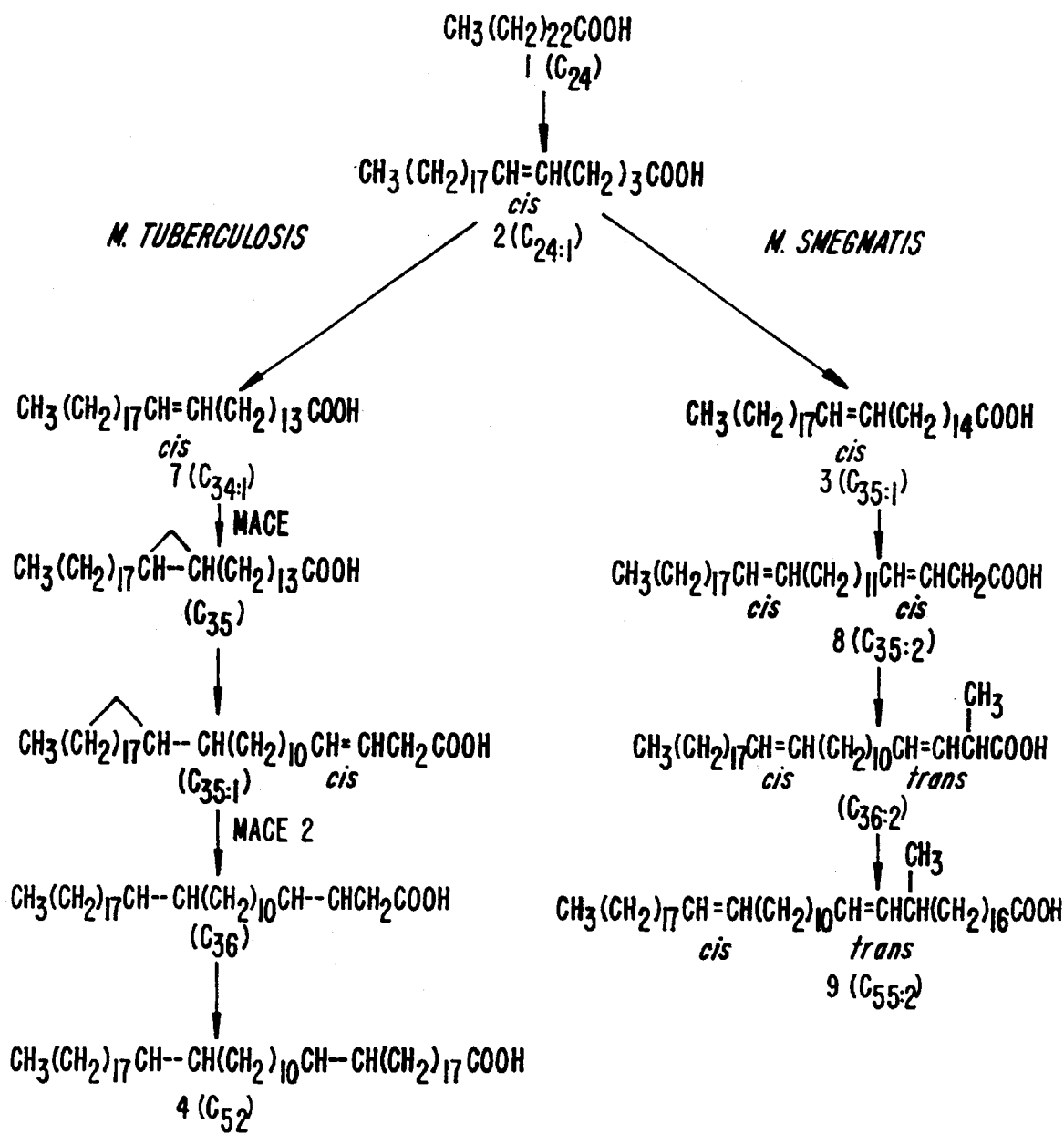
FIG. 1 shows a comparison of the proposed mycolic acid biosynthesis for pathogenic *Mycobacterium tuberculosis* and non-pathogenic *Mycobacterium smegmatis*. This figure illustrates how these pathways diverge at the cyclopropanation step.
Figure 3A:
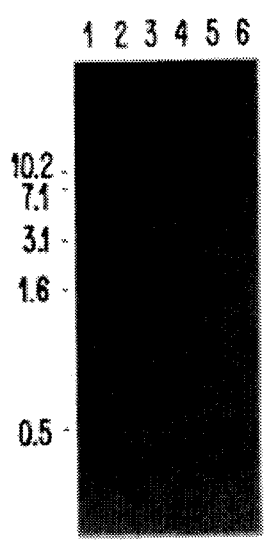
FIG. 3A–D are Southern Blots which illustrates the homology between cma (SEQ. ID. No. 2) and nucleic acid sequences in other pathogenic forms of mycobacterium, specifically *M. marinum* and *M. avium*.
Figure 3B:
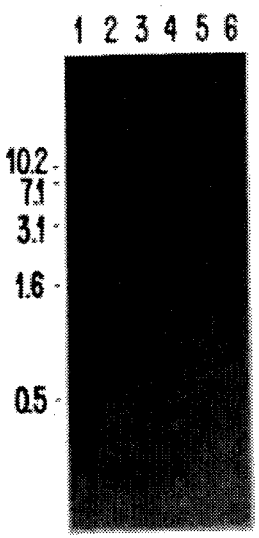
Figure 3C:
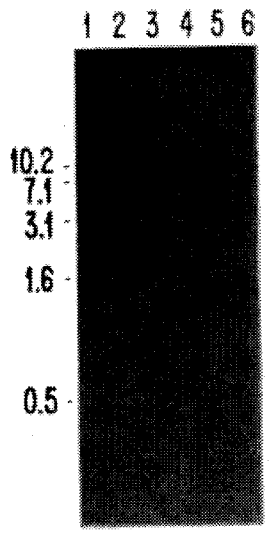
Figure 3D:
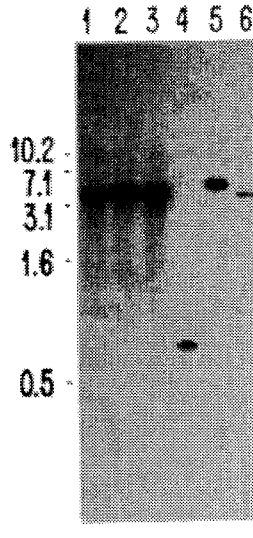

Sequence listing abbreviations for the twenty naturally occurring amino acids follow conventional usage. In the polypeptide notation used in such sequence listings, the left-hand direction is the amino terminal direction and the right-hand direction is the carboxy-terminal direction, also in accordance with standard usage and convention.

"NUCLEIC ACIDS" refers to either DNA or RNA. "Nucleic acid sequence" or "polynucleotide sequence" refers to single or double-stranded polymers of deoxyribonucleotide or ribonucleotide bases read from the 5' end to the 3' end. It includes self-replicating plasmids, infectious polymers of DNA or RNA and nonfunctional DNA or RNA.

"NUCLEIC ACID PROBES" or "OLIGONUCLEOTIDE PROBES" can be DNA or RNA fragments. DNA fragments can be prepared, for example, by digesting plasmid DNA, by use of PCR, or synthesis by either the phosphoramidite method or the triester method. Where a specific sequence for a nucleic acid probe is given, it is understood that the complementary strand is also identified and included. The complementary strand will work equally well in situations where the target is a double-stranded nucleic acid.

"SELECTIVELY HYBRIDIZING TO" refers to a nucleic acid probe that, under appropriate hybridization conditions, hybridizes, duplexes or binds only to a particular target DNA or RNA sequence when the target sequences are present in a preparation of total cellular DNA or RNA. "Complementary" or "target" nucleic acid sequences refer to those nucleic acids that selectively hybridize to a nucleic acid probe. Proper annealing conditions depend, for example, upon a probe's length, base composition, the number of mismatches and their position on the probe which must often be determined empirically. For discussions of nucleic acid probe design and annealing conditions, see, for example, Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., (ed.) Greene Publishing and Wiley-Interscience, New York (1987).

"STRINGENT CONDITIONS" refers to conditions under which a nucleic acid probe will hybridize substantially to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a complementary probe. Typically, stringent conditions will be those in which the salt concentration is at least about 0.2 molar at pH 7 and the temperature is at least about 60° C. for long sequences (e.g. greater than about 50 nucleotides) and at least about 42° C. for shorter sequences (e.g. 10 to 50 nucleotides).

"NUCLEIC ACID SEQUENCE ENCODING" refers to a nucleic acid which directs the expression of a specific protein or peptide. Such a nucleic acids sequence is deemed to include both the DNA strand sequence that is transcribed into RNA and the RNA strand sequence that is translated into protein. Also, such a nucleic acid sequence includes both the full length nucleic acid sequence and partial or variant nucleic acid sequences which encode the same protein.

"CONTROL SEQUENCE" refers to a DNA sequence or sequences that are capable, when properly attached to a desired coding sequence, of causing expression of the coding sequence. Such control sequences include at least promoters and, optionally, transcription termination signals. Often, control sequences are utilized as an "expression cassette," in which the control sequences are operably linked to the nucleic acid that is to be expressed.

"VECTOR" refers to nucleic acids that are capable of replicating in a selected host organism. Vectors include viral- or bacteriophage-based expression systems, autonomous self-replicating circular DNA (plasmids), and both expression and nonexpression vectors. Such vectors can replicate as an autonomous structure or, alternatively, can integrate into the host cell chromosome(s) and thus replicate along with the host cell genome.

"PLASMID" refers to an autonomous circular DNA molecule capable of replication in a cell, and includes both the expression and nonexpression types. Where a recombinant microorganism or cell culture is described as hosting an "expression plasmid," this includes both extrachromosomal circular DNA molecules and DNA that has been incorporated into the host chromosome(s).

"RECOMBINANT PROTEIN" or "RECOMBINANTLY PRODUCED PROTEIN" refers to a peptide or protein produced using recombinant DNA techniques. Host cells produce the recombinant protein because they have been genetically altered by the introduction of the appropriate nucleic acid that codes for the protein. Typically, the heterologous nucleic acid is introduced as part of an expression vector.

"REFERENCE SEQUENCE" describes the sequence relationships between two or more nucleic acids or polynucleotides. A "reference sequence" is a defined sequence used as a basis for a sequence comparison; a reference sequence can comprise a complete cDNA or gene sequence, such as the nucleic acid sequence of Seq. ID Nos. 2, 4, or 6, or can be a subset of a larger sequence, for example, as a segment of a full-length cDNA or gene sequence. Optimal alignment of sequences for aligning a "comparison window" can be conducted by the local homology algorithm of Smith and Waterman (1981) *Adv. Appl Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci.* (USA) 85:2444, or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.).

"SUBSTANTIAL IDENTITY" or "SUBSTANTIAL SEQUENCE IDENTITY" as applied to nucleic acids denotes a characteristic of a polynucleotide wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25–50 nucleotides. The percentage of sequence identity is calculated by comparing the reference sequence to the polynucleotide sequence, which may include deletions or additions which total 20 percent or less of the reference sequence over the window of comparison. The reference sequence may be a subset of a larger sequence, such as a segment or subsequence of the genes disclosed in this application. As applied to polypeptides, the terms "substantial identity" or "substantial sequence identity" mean that two peptide sequences, when optimally aligned—such as by the programs GAP or BESTFIT using default gap weights, share at least 80 percent sequence identity, preferably at least 90 percent sequence identity, more preferably at least 95 percent sequence identity. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions that are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

"SUBSTANTIALLY PURIFIED" or "ISOLATED," when referring to a polypeptide, means a chemical composition that is essentially free of other cellular components. The particular polypeptide is preferably in a homogeneous state, although it can be in either a dry form or in an aqueous solution. Purity and homogeneity are typically determined using analytical chemistry techniques such as polyacrylamide gel electrophoresis (PAGE) or high performance liquid chromatography (HPLC). A protein that is the predominant species present in a preparation is considered substantially purified. Generally, a substantially purified or isolated protein will comprise more than 80% of all macromolecular species present in the preparation. Preferably, the protein is purified to represent greater than 90% of all macromolecular species present. More preferably the protein is purified to be greater than 95%, and most preferably the protein is purified to essential homogeneity, wherein other macromolecular species are not detected by conventional techniques.

"SPECIFICALLY BINDS TO AN ANTIBODY" or "SPECIFICALLY IMMUNOREACTIVE WITH," when referring to a protein or peptide, refers to a binding reaction that is determinative of the presence of the protein in the presence of a heterogeneous population of proteins and other biologics. Thus, under designated immunoassay conditions, the specified antibodies bind to a particular protein and do not bind in a significant amount to other proteins present in the sample. Obtaining an antibody that specifically binds to a particular protein may require screening. A variety of immunoassay formats can be used to select antibodies specifically immunoreactive with a particular protein. For example, solid-phase enzyme-linked immunoassays (ELISAs) are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

DETAILED DESCRIPTION OF THE PREFERRED EMBODIMENTS

The present invention provides recombinant proteins and the isolated nucleic acids encoding such proteins for *Mycobacterium tuberculosis*. The most important of these recombinant proteins is the Mycolic Acid Cyclopropanating Enzyme or "MACE" (SEQ. ID No. 3). Since cyclopropanation of mycolic acids distinguishes pathogenic forms of mycobacteria from non-pathogenic forms, inhibition of MACE activity in pathogenic forms of mycobacteria, such as *Mycobacterium tuberculosis*, may hold the key to successfully fighting all forms of such pathogenic mycobacteria. With this in mind, the recombinant proteins and isolated nucleic acids of the present invention can be used in a number of applications, including nucleic acid probe and PCR assays to detect the presence of *M. tuberculosis* and assays for the design and selection of MACE inhibiting drugs.

A. Recombinant *M. tuberculosis* Proteins

1. Nature of The Recombinant *M. tuberculosis* Proteins

Three proteins, which are encoded by a 7.2 kb BamH1 fragment from the *M. tuberculosis* genome, are a subject of the present invention. SEQ ID No. 1 shows a nucleotide sequence from the 7.2 kb BamH1 fragment which encodes all three of these proteins. These three proteins include the MACE protein described in SEQ. ID No. 3 as well as two other proteins whose projected amino acid sequences are shown in SEQ. ID. Nos. 5 and 7. These three proteins are encoded by the three open reading frames found within the 7.2. kb BamH1 fragment and are all believed to relate to the biosynthesis of mycolic acids in *M. tuberculosis*.

The MACE protein (SEQ. ID No. 3) has 288 amino acids and a molecular weight of 32,460 daltons. The MACE protein functions to cyclopropanate long chain fatty acids in the putative biosynthetic pathway for *M. tuberculosis* mycolic acids shown in FIG. 1. The postulated intermediate in the biosynthesis of *M. tuberculosis* mycolic acids upon which the MACE protein acts is shown adjacent the abbreviation "MACE" in FIG. 1. Computer analysis of the MACE amino acid sequence reveals that it displays 33% homology to the cyclopropane fatty acid synthase of *E. coli* (SEQ. ID No. 9). See, Grogan and Cronan, *J. Bact.* 158:286 (1984). This homology of amino acid sequences is illustrated in FIG. 2, where the homologous amino acids have been darkened and the non-homologous amino acids have been left in regular type. The recombinant MACE protein of the present invention (SEQ. ID No. 3) also shows significant homology with the predicted amino acid sequence encoded by an nucleic acid sequence from the M. leprae genome sequencing project deposited in GenBank (SEQ ID No. 8). See, Eiglmeier et al., *Mol. Micro.* 7, 197(1993); Honore et al., *Mol Micro.* 7, 207(1993). On the DNA level, the two sequences are 55.2% identical, while on the protein level, as shown in FIG. 2, they are 59.5% identical. Although MACE and this particular *M. leprae* protein display significant homology, they have been shown to have different functions in mycolate biosynthesis. This particular *M. leprae* protein serves to introduce a cyclopropane to a later intermediate in the biosynthetic pathway as denoted by "MACE2" in the putative biosynthetic pathway of FIG. 1. It is noteworthy that, through hybridization techniques, the inventors were able to isolate the nucleic acid sequence encoding a second *M. leprae* protein which, in this instance, appears to have the same function as MACE.

In addition to the MACE protein, two additional proteins are encoded by open reading frames in close proximity to the open reading frame which encodes the MACE protein. The putative amino acid sequences for these additional proteins are shown in SEQ. ID Nos. 5 and 7. The first of these additional recombinant proteins, shown in SEQ. ID No. 5, has homology to known enzymes involved in the oxidative/reductive interconversions of a ketone and an alcohol. This protein is most homologous (30% identify over 188 amino acids) to actIII, β-ketoacyl reductase from *Streptomyces cinnamonesis* which is involved in chain elongation in polyketide biosynthesis. T.J. Arrowsmith et al., *Mol Gen. Genet.* 234, 254 (1992). This protein also scores significantly against many other proteins involved in reductive aspects of polyketide, fatty acids, and short-chain alcohol metabolism. This suggests that it plays a similar role in mycolic acid biosynthesis in *M. tuberculosis*.

The remaining recombinant protein, shown in SEQ ID. No. 7, is most similar to enzymes which operate in fatty acid catabolism or in steroid modification. This protein is most related (35% identical over 278 amino acids) to the trifunctional hydratase-dehydrogenase-epimerase from the yeast *Candida tropicalis* which is associated with peroxisomal degradation of fatty acids and related metabolites. Nuttley et al., *Gene* 69, 171(1988); Aitchison et al., *Gene* 105, 135(1991). This protein is also related to another enzyme, FOX2 from *Saccharomyces cereviasiae*, which also catalyzes the same three reactions, as well as to a 17-β-estradiol dehydrogenase from Pig. Hiltunen et al., *J. Biol. Chem.* 267, 6646(1992); Leenders et al., *Eur. J. Biochem.* 222, 221 (1994).

2. Expression of Recombinant *M. tuberculosis* Proteins

The present invention also provides methods for expressing recombinant *M. tuberculosis* proteins. These methods involve cloning the isolated nucleic acid sequences from *M. tuberculosis* into an appropriate expression vector, transforming the expression vector into host cells, and growing the host cells under conditions that lead to expression of the *M. tuberculosis* proteins of the present invention. In brief summary, the expression of natural or synthetic nucleic acids encoding *M. tuberculosis* proteins will typically be achieved by operably linking a protein encoding nucleic acid sequence to a control sequence promoter that functions in the host cell of choice to form an "expression cassette". Either constitutive or inducible promoters are suitable. This expression cassette is then typically incorporated in an expression vector. The vectors contain regulatory regions that cause the vector to replicate autonomously in the host cell, or else the vector can replicate by becoming integrated into the genomic DNA of the host cell. Typical expression vectors can also contain, as part of their control sequence, transcription and translation terminators, translation initiation sequences, and enhancers that are useful for regulating the amount of protein expression. To obtain high level expression of a cloned gene, it is desirable to construct expression vectors that contain, at minimum, a strong promoter to direct transcription, a ribosome binding site for translational initiation, and a transcription/translation terminator.

A variety of prokaryotic expression systems can be used to express recombinant *M. tuberculosis* proteins of the present invention. Examples of suitable host cells include *M. smegmatis, E. coli, Bacillus sps., Streptomyces sps.*, and the like. For each host cell, one employs an expression plasmid that contains appropriate control sequences to that direct transcription and translation in the chosen host organism. Such control sequences typically include a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway described by Yanofsky, C. (1984) *J. Bacteriol.* 158:1018–1024 and the leftward promoter of phage-lambda (pλ) as described by Herskowitz and Hagen (1980) *Ann. Rev. Genet.* 14: 399–445. Several commercial manufacturers of molecular biology reagents sell prokaryotic expression vectors that have been optimized for high levels of heterologous gene expression. See, e.g., product catalogs from Stratagene Cloning Systems, La Jolla Calif.; Clontech Laboratories, Palo Alto Calif.; Promega Corporation, Madison Wis.

A preferred prokaryotic expression system for the present invention is a mycobacterial overexpression system which includes the hsp60 promoter sequence from *M. tuberculosis*, a hygromycin shuttle plasmid, p16R1, and an *M. smegmatis* host cell. This overexpression system is described in greater detail in Example 2 and FIG. 5. This type of overexpression system is preferred, among other reasons, because it incorporates mycobacterial components similar to those found in naturally occurring *M. tuberculosis*.

Although prokaryotic expression systems are preferred because *M. tuberculosis* is a prokaryote, a variety of eukaryotic expression systems are known to those of skill in the art, such as yeast, insect cell lines, bird, fish and mammalian cells, and can be used in the present invention. Several commercial manufacturers of molecular biology reagents sell expression vectors that are suitable for use in different eukaryotic host cells. See, product catalogs from Stratagene Cloning Systems, La Jolla Calif.; Clontech Laboratories, Palo Alto Calif.; Promega Corporation, Madison Wis.

Yeast cells are an example of a eukaryotic expression system. The synthesis of heterologous proteins in yeast is well known. *Methods in Yeast Genetics*, Sherman, F., et al., Cold Spring Harbor Laboratory, (1982) is a well recognized work describing the various methods available to produce the protein in yeast. Suitable vectors for expression in yeast usually have expression control sequences, such as promoters, including 3-phosphoglycerate kinase or other glycolytic enzymes, and an origin of replication, termination sequences and the like as desired. For instance, suitable vectors are described in Botstein, et al., 1979, *Gene,* 8:17–24; Broach, et aL, 1979, *Gene,* 8:1 21–133. The *M. tuberculosis* proteins, once expressed, can be isolated from yeast by lysing the cells and applying standard protein isolation techniques to the lysates. The monitoring of the purification process can be accomplished by using Western blot, radioimmunoassay or other standard immunoassay techniques.

3. Purification of *M. tuberculosis* Proteins

The recombinant proteins of the present invention can be purified by standard techniques well known to those of skill in the art. Typically, the host cells are lysed (e.g., by sonication) and the protein is then substantially purified using standard techniques such as selective precipitation with ammonium sulfate, column chromatography, immunopurification methods and others. See, e.g., R. Scopes, *Protein Purification: Principles and Practice*, Springer-Verlag: New York (1982), which is incorporated by reference. In one preferred embodiment, MACE protein is purified using a modification of the method for purifying the cyclopropane fatty acid synthase from *Escherichia coli* described in Taylor and Cronan, *Biochemistry* 18,3292–3300(1979). To implement this modification of the Taylor and Cronan method, ammonium sulfate purified MACE, sucrose and a suspension of lipid from wild type *M. smegmatis* are mixed in a phosphate buffer, incubated, and centrifuged. This preferred modification of the Taylor and Cronan method is described in greater detail in Example 4. As another alternative, one can raise antibodies against *M. tuberculosis* proteins and use the antibodies for immunoprecipitation or affinity chromatography using standard methods. If the protein is produced as a fusion protein, in which the *M. tuberculosis* moiety is fused to non-*M. tuberculosis* amino acids, the desired protein can be released by digestion with an appropriate proteolytic enzyme.

The purity and activity of a MACE isolate can be tested using an in vitro assay. In such an in vitro assay, the MACE isolate is added to a suitable substrate, such as the $C_{34}$ meromycolate intermediate from *M. tuberculosis* shown in FIG. 1, then incubated and tested for cyclopropanation of the substrate. Testing for cyclopropanation of the substrate can be accomplished in a number of ways including thin layer chromatography (TLC) and nuclear magnetic resonance (NMR). The protocol to conduct such tests for cyclopropanation are described in greater detail in Examples 1, 3 and 4.

B. Isolated *M. tuberculosis* Nucleic Acids

1. Description of Isolated *M. tuberculosis* Nucleic Acids

The nucleic acids of the present invention are identical to or show substantial sequence identity to the nucleic acid sequences of SEQ ID No. 1, 2, 4, or 6. The native forms of these nucleic acids originate from a 7.2 kb BamH1 fragment in the *M. tuberculosis* genome. As schematically shown in the restriction map of FIG. 4, this 7.2 kb BamH1 fragment has three open reading frames, identified in that figure as cma (SEQ ID No. 2), ORF2 (SEQ ID No. 4) and ORF3 (SEQ. ID No. 6). The cma open reading frame (SEQ ID No. 2) encodes for the MACE protein. The ORF2 open reading frame (SEQ ID No. 4) encodes for the protein shown in SEQ. ID No. 3, which has homology to enzymes involved in the oxidative/reductive interconversions of a ketone and an alcohol. The final open reading frame shown in FIG. 4, ORF 3 (SEQ. ID No. 6), encodes the protein shown in SEQ. ID No. 5, which has homology to enzymes operating in fatty acid catabolism or in steroid modification. As previously noted, the nucleic acids of the present invention include not only native sequences but also homologue sequences which would typically hybridize to the native sequences under stringent hybridization conditions. The single letter abbreviations shown in FIG. 4 denote restriction endonucleases, specifically BamH1 ("B"), PstI ("P"), NotI ("N"), EcoRI ("E") and EcoRV ("EV").

Since the MACE protein encoded by the cma open reading frame (SEQ. ID No. 3) is responsible for cyclopropanation of mycolic acids in *M. tuberculosis*, one would expect homologous reference sequences to be found in other pathogenic forms of mycobacteria which cyclopropanate their mycolic acids. This expected homology was found by the inventors through the use of hybridization techniques and is evidenced by the Southern blots shown in FIGS. 3A–3D. Each of the Southern blots shown in FIGS. 3A–3D has six lanes corresponding, respectively, to 1 μg samples of DNA from: (1) *M. tuberculosis* H37Ra, (2) *M. tuberculosis* H37Rv, (3) *M. tuberculosis* Erdman, (4) *M. marinum*, (5) *M. avium* serovar 4 and (6) *M. smegmatis* $mc^2155$. FIG. 3A shows each of these six samples probed with a 1.0 kb fragment of cma (SEQ ID No. 3). FIG. 3B shows each of these six samples probed with a 994 bp fragment of ORF2 (SEQ. ID No. 4). FIG. 3C shows each of these six samples probed with an 760 bp fragment of ORF3 (SEQ. ID No. 6). Finally, FIG. 3D shows each of these six samples probed with an 823 bp fragment of InhA. Molecular size standards are shown at the left in kilobases (kb). Hybridization was done at 62° C. and the blots were washed under stringent conditions.

Hybridization techniques were also used to find homology between cma and a nucleic acid sequence from *M. leprae*. Specifically, the inventors were able to use two primers for cma (SEQ. ID No. 10 and 11) to PCR amplify a nucleic acid sequence from *M. leprae*. The amplified nucleic acid sequence from *M. leprae* was then cloned and found to express a protein which was substantially homologous to MACE.

2. Isolation of *M. Tuberculosis* Nucleic Acids

The nucleic acid compositions of this invention, whether genomic DNA, RNA, or a hybrid of the various combinations, may be isolated from natural sources or may be synthesized in vitro. Moreover, the nucleic acids of the present invention can be found in transformed or transfected whole cells, in a transformed or transfected cell lysate, or in a partially purified or substantially pure form.

Techniques for manipulating the other nucleic acids of the present invention, such as those techniques used for subcloning the nucleic acids into expression vectors, labelling probes, nucleic acid hybridization, and the like are described generally in Sambrook et aL, *Molecular Cloning—A Laboratory Manual* (2nd Ed.), Vol. 1–3, Cold Spring Harbor Laboratory, Cold Spring Harbor, N.Y., 1989, which is incorporated by reference.

Various methods for isolating the nucleic acids of the present invention are available. For example, one can isolate DNA from a genomic library by using labeled oligonucleotide probes that have nucleotide sequences complementary to the *M. tuberculosis* sequences of the present invention. One can also use full-length probes or oligonucleotide probes that are based on specific subsequences of these genes. One can use such probes directly in hybridization assays to isolate particular nucleic acids or one can use amplification methods such as polymerase chain reaction ("PCR").

Methods for preparing genomic libraries are also well known to those of skill in the art. See, e.g., Sambrook, supra. Typically, one can prepare a genomic library by extracting DNA from tissue and either mechanically shearing or enzymatically digesting the DNA to yield fragments of about 12–20 kb, or longer if a cosmid is used as the cloning vector. Fragments of the desired size can be purified by density gradient centrifugation or gel electrophoresis. The fragments are then cloned into suitable cloning vectors, such as bacteriophage lambda vectors or cosmids. If phage or cosmids are used, one then packages the DNA in vitro, as described in Sambrook, supra. Recombinant phage or cosmids can be analyzed by plaque hybridization as described in Benton and Davis, (1977) *Science* 196:180–182. Alternatively, colony hybridization can be carried out as generally described in Grunstein et al. (1975) *Proc. Natl Acad. Sci. USA.* 72:3961–3965.

Standard techniques are used to screen the cDNA or genomic DNA libraries to identify those vectors that contain a nucleic acid encoding MACE and the other proteins of the present invention. For example, Southern blots are utilized to identify those library members that hybridize to nucleic acid probes derived from the nucleotide sequences shown in SEQ. ID Nos. 2, 4 and 6. Such probes might take the form of SEQ. ID Nos. 10 through 15. See, e.g., Sambrook, supra.

Alternatively, one can prepare nucleic acids by using any of various methods of amplifying target sequences, such as PCR. For example, one can use PCR to amplify nucleic acid sequences of the present invention directly from mRNA, genomic DNA or from genomic DNA libraries. Briefly, to use PCR to isolate the nucleic acids of the present invention from genomic DNA, one synthesizes oligonucleotide primer pairs, the first of which is complementary to one strand 5' of the desired sequence and the other of which is complementary to the opposite strand 3' of the sequence to be amplified. One can select primers to amplify the entire region that codes for a full-length polypeptide or amplify smaller DNA segments that code for part of the polypeptide. Suitable primer pairs for amplification of the cma gene (SEQ. ID No. 2) are shown in SEQ ID Nos. 10 and 11. The primers shown in SEQ. ID Nos. 12 and 13 would be appropriate for amplifying the ORF2 nucleotide sequence (SEQ. ID No. 4). The primers shown in SEQ. ID Nos. 14 and 15 would be appropriate for amplifying the ORF3 nucleotide sequence. PCR is then carried out using the appropriate two primers. See, e.g., *PCR Protocols: A Guide to Methods and Applications.* (Innis, M, Gelfand, D., Sninsky, J. and White, T., eds.), Academic Press, San Diego (1990). Amplified fragments can be used as hybridization probes to identify other nucleic acids of the present invention or can be used to evaluate the presence of appropriate sequences directly.

Other methods known to those of skill in the art can also be used to isolate DNA encoding the proteins of the present invention. See, e.g., Sambrook, supra., for a description of other techniques that are useful for isolating DNA that codes for specific polypeptides.

C. Detection of *M. tuberculosis* Using Nucleic Acid Assays

To permit the clinician to determine whether a patient has a *M. tuberculosis* bacteria in their bodies, the present invention provides assays for detecting DNA and RNA molecules that code for the tuberculosis proteins of the present invention, particularly MACE.

A variety of nucleic acid hybridization formats are available for this purpose including Northern blots, Southern blots, sandwich assays and competition or displacement assays. Hybridization techniques are generally described in "*Nucleic Acid Hybridization, A Practical Approach,*" Hames, B.D. and Higgins, S.J. (eds.), IRL Press, 1985; Gall and Pardue (1969) *Proc. Natl Acad. Sci. USA.* 63: 378–383; and John et al. (1969) Nature 223: 582–587.

Suitable methods for Northern blots are described in, for example, Sambrook, supra. and Chomczynski and Sacchi (1987) Anal Biochem. 162:156–159. Briefly, in a Northern blot, RNA is isolated from a cell sample using an extraction solution that releases the RNA from the cells while preventing degradation of the RNA. A commonly-used extraction solution contains a guanidinium salt. The RNA is purified from the extraction solution, such as by phenol-chloroform extraction followed by ethanol precipitation. The RNA is then size-fractionated by electrophoresis, after which the RNA is transferred from the gel to a nitrocellulose or nylon membrane. Labeled probes are used to ascertain the presence or absence of *M. tuberculosis*-encoding mRNA.

In a Southern blot, digested genomic target DNA is run on agarose slab gels in buffer and transferred to membranes. Hybridization is carried out using nucleic acid probes, such as those of SEQ. ID Nos. 2, 4, 6 and 10 through 19. The probe can be full length to code for a particular protein, such as MACE, or less than full length. Shorter probes should be empirically tested for specificity. Preferably nucleic acid probes are 20 bases or longer in length. See, Sambrook, et al. for methods of selecting nucleic acid probe sequences for use in nucleic acid hybridization. Visualization of the hybridized portions on the Southern blot allows the qualitative determination of the presence or absence of DNA encoding *M. tuberculosis* proteins.

Sandwich assays are commercially useful hybridization assays for detecting or isolating nucleic acid sequences. These assays are easily automated, which results in a more cost-effective and sometimes more accurate assay. Sandwich assays utilize a "capture" nucleic acid probe that is covalently linked to a solid support and a labeled "signal" nucleic acid probe that is in solution. The clinical sample provides the "target" nucleic acid. The "capture" nucleic acid and "signal" nucleic acid probes each hybridize to the target nucleic acid to form a "sandwich" hybridization complex. To be effective, the signal nucleic acid probe cannot hybridize to the capture nucleic acid probe. Detection of a hybridization complex usually requires binding of the signal probe to a duplex of target and capture nucleic acids. Typically, such binding occurs through ligand and anti-ligand interactions as between a ligand-conjugated probe and an anti-ligand conjugated with a signal probe. The label can also allow indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label. Tijssen, P., "Practice and Theory of Enzyme Immunoassays," *Laboratory Techniques in Biochemistry and Molecular Biology*, Burdon, R.H., van Knippenberg, P.H., Eds., Elsevier (1985), pp. 9–20.

The sensitivity of the hybridization assays can be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q Beta Replicase systems. Amplification methods permit one to detect the presence or absence of *M. tuberculosis* nucleic acids using only a very small sample. Furthermore, amplification methods are especially amenable to automation.

An alternative means for determining the level at which an *M. tuberculosis* gene is expressed is in situ hybridization. In situ hybridization assays are well known and are generally described in Angerer et al. (1987) *Methods Enzymol.* 152: 649–660. In an in situ hybridization assay, cells are fixed to a solid support, typically a glass slide. If DNA is to be probed, the cells are denatured with heat or alkali. The cells are then contacted with a hybridization solution at a moderate temperature to permit annealing of labeled probes specific to *M. tuberculosis*-encoding nucleic acids.

Oligonucleotides are preferably used as probes in the assays of the present invention, although longer fragments that comprise most or all of an *M. tuberculosis* gene, such as cma (SEQ. ID No. 3), are also suitable. Suitable oligonucleotide probes are generally between about 10 and 100 nucleotides in length and are capable of selectively hybridizing, under stringent hybridizing conditions, to a nucleotide target region in the assay sample (i.e., a specific subsequence of a *M. tuberculosis* nucleic acid). The degree of homology required for detectable binding with the target nucleic acids will vary in accordance with the stringency of the hybridization medium and/or wash medium. The degree of homology will optimally be 100 percent; however, it should be understood that minor variations in the two nucleic acid sequences may be compensated for by reducing the stringency of the hybridization and/or wash medium. Thus, despite the lack of 100 percent homology under reduced conditions of stringency, functional probes having minor base differences from their nucleic acid targets are possible. Therefore, under hybridization conditions of reduced stringency, it may be possible to modify up to 60% of a given oligonucleotide probe while maintaining an acceptable degree of specificity. In addition, analogs of nucleotides may be substituted within the probe for naturally occurring nucleotides.

Suitable oligonucleotide probes include synthetic oligonucleotides, cloned DNA fragments, PCR products and RNA molecules. The nature of the probe is not important, provided that it hybridizes specifically to target *M. tuberculosis* nucleic acids under stringent hybridization conditions and not to other nucleic acids. To obtain large quantities of DNA or RNA probes, one can either clone the desired sequence using traditional cloning methods, such as described in Sambrook et al., supra or one can produce the probes by chemical synthesis using commercially available DNA synthesizers. An example of using traditional cloning methods would involve insertion of all or part of the cDNA into a replication vector, and transformation of a bacterial host. The probes would then be purified from the host cell by lysis, nucleic acid extraction, treatment with selected restriction enzymes and further isolation by gel electrophoresis. Oligonucleotide probes can also be chemically synthesized using commercially available methods and equipment. For example, the solid phase phosphoramidite triester method first described by Beaucage and Carruthers [(1981) *Tetrahedron Lett.* 22:1859–1862] is suitable. This method can be used to produce relatively short probes of between 10 and 50 bases. The triester method described by Matteucci et al. [(1981) *J. Am. Chem. Soc.*, 103:3185] is also suitable for synthesizing oligonucleotide probes. Conveniently, one can use an automated oligonucleotide synthesizer, such as the Model 394 DNA/RNA Synthesizer from Applied Biosystems (Foster City, Calif.), using reagents supplied by the same company. After synthesis, the synthetic oligonucleotides can be purified either by native acrylamide gel electrophoresis or by anion-exchange HPLC as described in, for example, Pearson and Regnier (1983) *J. Chrom.* 255:137–149. The sequence of the synthetic oligonucleotide can be verified using the chemical degradation method of Maxam, A.M. and Gilbert, W. (1980) In Grossman, L. and Moldave, D., eds. Academic Press, New York, *Methods in Enzymology*, 65:499–560.

Probes can be comprised of natural nucleotides or known analogs of the natural nucleotides, including those modified to bind labeling moieties. Oligonucleotide probes that comprise thionucleotides, and thus are resistant to nuclease cleavage, are also suitable. One can use probes that are full length coding regions or probes that hybridize to a specific subsequences. Shorter probes should be empirically tested for specificity. Preferably, nucleic acid probes are 15 nucleotides or longer in length, although oligonucleotide probe lengths of between about 10 and 100 nucleotides or longer are appropriate. Sambrook, supra. describes methods for selecting nucleic acid probe sequences for use in nucleic acid hybridization.

For purposes of this invention, the signal probes are typically labeled so that one can detect whether the probe has bound to a target nucleic acid. Signal probes can be labeled by any one of several methods typically used to detect the presence of hybrid polynucleotides. The most common method of detection is the use of autoradiography for probes labeled with $^3H$, $^{125}I$, $^{35}S$, $^{14}C$, $^{32}P$, or the like. The choice of radioactive isotope depends on research preferences due to ease of synthesis, stability, and half lives of the selected isotopes. Other labels include ligands, which bind to antibodies labeled with fluorophores, chemiluminescent agents and enzymes. Alternatively, probes can be conjugated directly with labels such as fluorophores, chemiluminescent agents or enzymes. The choice of label depends on sensitivity required, ease of conjugation with the probe, stability requirements and available instrumentation.

The choice of label dictates the manner in which the label is bound to the probe. Radioactive probes are typically made using commercially available nucleotides containing the desired radioactive isotope. The radioactive nucleotides can be incorporated into probes, for example, by using DNA synthesizers, by nick translation or primer extension with DNA polymerase I, by tailing radioactive nucleotides to the 3' end of probes with terminal deoxynucleotidyl transferase, by incubating single-stranded M13 plasmids having specific inserts with the Klenow fragment of DNA polymerase in the presence of radioactive deoxynucleotides, dNTP, by transcribing from RNA templates using reverse transcriptase in the presence of radioactive deoxynucleotides, dNTP, or by transcribing RNA from vectors containing specific RNA mycobacterial promoters (e.g., hsp60 promoter) using the corresponding RNA polymerase in the presence of radioactive ribonucleotides rNTP. The probes can be labeled using radioactive nucleotides in which the isotope resides as a part of the nucleotide molecule, or in which the radioactive component is attached to the nucleotide via a terminal hydroxyl group that has been esterified to a radioactive component such as inorganic acids, e.g., $^{32}$p phosphate or $^{14}$C organic acids, or esterified to provide a linking group to the label. Base analogs having nucleophilic linking groups, such as primary amino groups, can also be linked to a label.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase, as described in Renz. M., and Kurz, K., *Nucl. Acids Res.* 12:3435–3444 (1984). Synthetic oligonucleotides have been coupled directly to alkaline phosphatase. Jablonski, E., et al., *Nucl. Acids Res.* 14:6115–6128 (1986); and Li P., et al., *Nucl. Acids Res.* 15:5275–5287 (1987).

Enzymes of interest as labels will typically be hydrolases, such as phosphatases, esterases, glycosidases, oxidoreductases and peroxidases. Fluorescent compounds include fluorescein and its derivatives, rhodamine and its derivatives, dansyl, umbelliferone, etc. Chemiluminescers include luciferin and 2,3-dihydrophthalazinediones, e.g., luminol.

The oligonucleotide or polynucleotide acid probes of this invention can be included in a kit to determine the presence and level of *M. tuberculosis* DNA or mRNA in cells of a human sample. Such a kit would typically include a stable preparation of labeled probes specific for *M. tuberculosis* nucleic acids of the present invention, hybridization solution in either dry or liquid form for the hybridization of target and probe polynucleotides, a solution for washing and removing undesirable and nonduplexed polynucleotides, a substrate for detecting the labeled duplex and, optionally, an instrument for the detection of the label. The probe components include combinations of probes in dry form, such as lyophilized nucleic acid, or in precipitated form, such as alcohol precipitated nucleic acid, or in buffered solutions. The label can be any of the labels previously described. The various reagents for the detection of labeled probes and other miscellaneous materials for the kit, such as instructions, positive and negative controls, and containers for conducting, mixing and reacting the various components, would typically complete the assay kit.

For a sandwich assay, such a kit would typically include a first component for the collection of samples from patients, vials for containment, and buffers for the dispersement and lysis of the sample. A second component typically contains media in either dry or liquid form for the hybridization of target and probe polynucleotides, as well as for the removal of undesirable and nonduplexed forms by washing. A third component includes a solid support upon which is fixed or to which is conjugated unlabeled nucleic acid probe(s) that is (are) complementary to a *M. tuberculosis* nucleic acid. In the case of multiple target analysis, more than one capture probe, each specific for its own *M. tuberculosis* nucleic acid target region, will be applied to different discrete regions of the solid support. A fourth component contains labeled probe that is complementary to a second and different region of the same *M. tuberculosis* nucleic acid strand to which the immobilized, unlabeled nucleic acid probe of the third component is hybridized.

Assay test protocols for use in this invention are those of convention in the field of nucleic acid hybridization and include both single phase, where the target and probe polynucleic acids are both in solution, and mixed phase hybridizations, where either the target or probe polynucleotides are fixed to an immobile support. The assay test protocols are varied and are not to be considered a limitation of this invention. A general review of hybridization can be had from a reading of *Nucleic Acid Hybridization: A Practical Approach*, Hames and Higgins, eds., IRL Press, (1985); and Meinkoth and Wah, *Analytical Biochemistry*, pp. 238, 267–284 (1984). Mixed phase hybridizations are preferred.

D. Use of MACE In An Assay To Test For Inhibition Of Enzymatic Activity

Since cyclopropanation of mycolic acids distinguishes forms of pathogenic mycobacteria, such as *M. tuberculosis*, from forms of non-pathogenic forms of mycobacteria, such as *M. smegmatis*, this cyclopropanation step is a logical target for the design of therapeutics to combat pathogenic forms of mycobacteria. Such an assay would typically involve addition of a prospective therapeutic to a purified preparation of enzymatically active MACE. After a suitable incubation period in the presence of the appropriate substrates and cofactors, mycolic acids would be extracted from the sample and chemically analyzed to determine if mycolic acids were being cyclopropanated to a lesser extent than in a control sample. The MACE for such assays could be obtained, for example, from whole cells, crude cell-free extracts from overexpressing clones or purified enzyme from overexpressing clones.

An alternative to this approach would be to use the *M. smegmatis* clone described in Example 1 which carries the recombinant DNA sequence expressing MACE. After exposure of this clone to a prospective therapeutic, the mycolic acids would be extracted from the mycobacterial clone and analyzed by silver ion chromatography for the presence of cyclopropanes. This alternative approach is described in greater detail in Examples 3 and 4.

E. Production Of Antibodies Specific to *M. tuberculosis* Proteins

A further aspect of the present invention is the production of antibodies which are specifically immunoreactive with proteins of *M. tuberculosis*, particularly MACE (SEQ. ID No. 3). A number of immunogens may be used to produce antibodies specifically immunoreactive with *M. tuberculosis* proteins. Recombinant protein is the preferred immunogen for the production of monoclonal or polyclonal antibodies. Naturally occurring protein may also be used either in pure or impure form. Synthetic peptides made using the protein sequences previously described (e.g., SEQ. ID Nos. 3, 5 and 7) may also be used as an immunogen for the production of antibodies to the protein. Recombinant protein can be expressed in eukaryotic or prokaryotic cells and purified as generally described above. The purified protein is then injected into an animal capable of producing antibodies. Either monoclonal or polyclonal antibodies may be generated.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the *M. tuberculosis* protein. When appropriately high titers of antibody to the immunogen are obtained, blood is collected from the animal and antisera is prepared. Further fractionation of the antisera to enrich for antibodies reactive to the protein can be done if desired.

Monoclonal antibodies may be obtained by various techniques familiar to those skilled in the art. Briefly, spleen cells from an animal immunized with a desired antigen are immortalized, commonly by fusion with a myeloma cell. See, Kohler and Milstein, *Eur. J. Immunol* 6:511–519 (1976), which is incorporated by reference. Alternative methods of immortalization include transformation with Epstein Barr Virus, oncogenes, retroviruses or other methods well known in the art. Colonies arising from single immortalized cells are screened for production of antibodies of the desired specificity and affinity for the antigen. Yield of the monoclonal antibodies produced by such cells may be enhanced by various techniques, including injection into the peritoneal cavity of a vertebrate host. Alternatively, one may isolate DNA sequences which encode a monoclonal antibody or a binding fragment by screening a DNA library from human B cells according to the general protocol outlined by Huse, et aL (1989) *Science* 246:1275–1281.

Methods of production of synthetic peptides are known to those of skill in the art. Briefly, the predicted immunogenic regions of the desired *M. tuberculosis* protein sequences are identified. Peptides, preferably at least 10 amino acids in length, are synthesized corresponding to these regions and the peptides are conjugated to larger protein molecules for subsequent immunization. Preferably, peptide sequences corresponding to unique regions of an *M. tuberculosis* protein are used to generate antibodies specifically immunoreactive with the potassium channel proteins. Examples of such peptides are depicted in Seq. ID Nos. 3, 5 and 7. Production of monoclonal or polyclonal antibodies is then carried out as described above.

F. Immunoassays To Detect M. Tuberculosis Proteins

The specific antibodies of the present invention can be used in an immunoassay to detect the presence of *M. tuberculosis* proteins. For a review of immunological and immunoassay procedures in general, see *Basic and Clinical Immunology* 7th Edition, D. Stites and A. Terr ed. (1991).

The immunoassays of the present invention typically take the form of either competitive or non-competitive assays. For a general review of such immunoassay formats, one can consult *Enzyme Immunoassay*, E.T, Maggio, ed., CRC Press, Boca Raton, Fla. (1980); "Practice and Theory of Enzyme Immunoassays," P. Tijssen, *Laboratory Techniques in Biochemistry and Molecular Biology*, Elsevier Science Publishers B.V. Amsterdam (1985); and, Harlow and Lane, *Antibodies, A Laboratory Manual*, supra, each of which is incorporated by reference.

In a competitive binding immunoassay for the present invention, the *M. tuberculosis* protein present in the sample competes with labeled protein for binding to a specific binding agent, for example, an antibody specifically reactive with the *M. tuberculosis* protein. The binding agent may be bound to a solid surface to effect separation of bound labeled protein from the unbound labeled protein. Alternately, the competitive binding assay may be conducted in liquid phase and any of a variety of techniques known in the art may be used to separate the bound labeled protein from the unbound labeled protein. Following separation, the amount of bound labeled protein is determined. The amount of *M. tuberculosis* protein present in the sample is inversely proportional to the amount of labeled protein binding.

Alternatively, a homogenous competitive binding immunoassay may be performed in which a separation step is not needed. In these immunoassays, the label on the protein is altered by the binding of the protein to its specific binding agent. This alteration in the labeled protein results in a decrease or increase in the signal emitted by label, so that measurement of the label at the end of the immunoassay allows for detection or quantification of the *M. tuberculosis* protein.

The presence of *M. tuberculosis* proteins may also be determined by a variety of noncompetitive immunoassay methods. For example, a two-site, solid phase sandwich immunoassay can be used. In this type of assay, a binding agent for the protein, for example an antibody, is attached to a solid phase. A second protein binding agent, which binds the protein at a different site and may also be an antibody, is labeled. After binding at both sites on the protein has occurred, the unbound labeled binding agent is removed and the amount of labeled binding agent bound to the solid phase is measured. The amount of labeled binding agent bound is directly proportional to the amount of *M. tuberculosis* protein in the sample.

Western blot analysis can also be done to determine the presence of *M. tuberculosis* proteins in a sample. Electrophoresis is carried out, for example, on a tissue sample suspected of containing the *M. tuberculosis* protein. Following electrophoresis to separate the *M. tuberculosis* proteins and transfer of the *M. tuberculosis* proteins to a suitable solid support, such as a nitrocellulose filter. The solid support is then incubated with an antibody reactive with the *M. tuberculosis* protein. This antibody may be labeled or, alternatively, it may be detected by subsequent incubation with a second labeled antibody that binds to the primary antibody.

The present invention also embraces kits for detecting the presence of specific *M. tuberculosis* proteins in tissue or blood samples. These kits typically include at least a container with antibodies specifically immunoreactive with the *M. tuberculosis* protein and instructional material for performing the test. The kit may also contain other components, such as the *M. tuberculosis* proteins themselves, controls, buffer solutions and secondary antibodies. Kits for detecting antibodies to *M. tuberculosis* proteins typically include at least a container with *M. tuberculosis* proteins and instructional material. Such a kit may also include other materials, such as secondary antibodies and labels as previously described in connection with nucleic acid hybridization assays.

EXAMPLES

Example 1: Cloning, Expression and Isolation of cma in *M. smegmatis*

A genomic cosmid library of *M. tuberculosis* H37Ra was constructed in pYUB18, an *E. coli*-mycobacterium shuttle vector. See, S.B. Snapper et al., *Proc. Natl. Acad. Sci. USA* 85, 6987(1988). This library was used to transform *M.* smegmatis mc²155 to kanamycin resistance. Both *M. smegmatis* mc²155 and pYUB18 were provided by William R. Jacobs, Albert Einstein College of Medicine. H37Ra DNA (100pg) was partially digested with Sau3AI and size-fractionated by 0.4% agarose gel electrophoresis. Fragments greater than 20 kb were excised, electroeluted, precipitated and ligated directly to alkaline-phosphatase treated pYUB18. They were then packaged using GigaPak Gold packaging extracts (Stratagene Cloning Systems, LaJolla, Calif.). The packaged material was used to infect *E. coli* DH5α. Approximately 15,000 primary transformants were scraped from plates and pooled before growing up overnight and extracting cosmid DNA.

The purified methyl esters of mycolic acids were examined from 697 independent clones by base hydrolysis followed by acidification and extraction with ether. Selective precipitation of methyl mycolates from crude mixtures has recently been described in M.E. Hamid et al., *J. Gen. Microbiol* 139, 2203 (1993) and this technique was used to remove contaminating lipids. Specifically, fresh transformants of mc²155 were selected off 7H11 agar plates containing 25 µg/ml kanamycin and used to inoculate 2ml cultures in 24-well plates containing 7H9 media with OADC, 0.05% Tween 80 and kanamycin (25 µg/ml). These cultures were grown for 48–72 hours before removing 1 ml from each well for mycolate analysis (the remainder was frozen at −80° C.). The 1 ml samples were transferred to PTFE capped vials and centrifuged at 1500 rpm for 10 minutes before aspirating the excess media. Toluene (1 ml) was added followed by a 1:1 mixture of methanol and 30% aqueous potassium hydroxide (1 ml). The vials were sealed and heated for at least 12 hours at 75° C. After cooling on ice, 250 µl of concentrated hydrochloric acid was added to each sample and each sample was extracted with approximately 2 ml of diethyl ether. The aqueous layer was removed and the ether washed with 1 ml of distilled water which was also removed. The ether layer was evaporated under a stream of argon before adding dichloromethane (0.5 ml), catalyst solution (0.5 ml)(sodium hydroxide, 0.8 g, tetrabutylammonium hydrogen sulfate, 3.39 g in 100 ml of distilled water) and methyl iodide (25 µl). The samples were allowed to sit with periodic vortexing for about an hour before the dichloromethane layer was removed to a microcentrifuge tube and evaporated. Toluene (200 µl) and acetonitrile (100 µl) were added to each sample and they were vortexed until the pellet redissolved. Acetonitrile (200 µl) was added and the samples were placed at 4° C. for two hours before spinning at 14,000 rpm for 10 minutes and removing the supernatant. The pellets were air-dried and then redissolved in a small volume (ca 20 µl) of benzene before spotting 0.5 µl onto TLC plates.

Figure 7A:
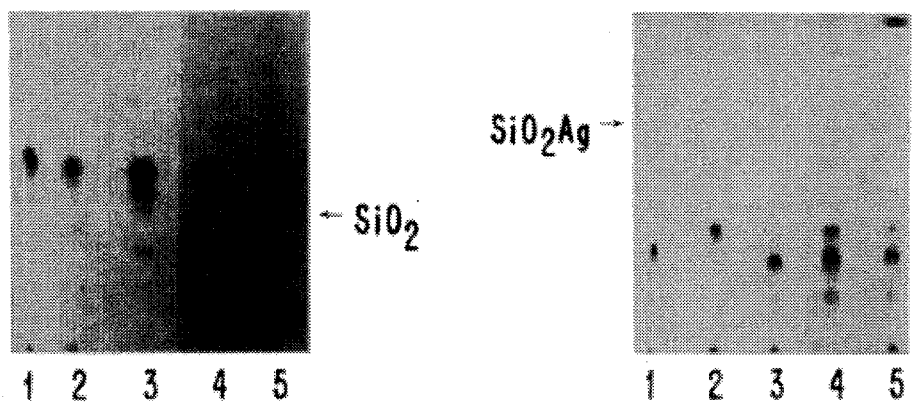
FIG. 7A–B shows the TLC results which were used to confirm that the *M. smegmatis* clone described in Example 1 produced MACE (SEQ ID No. 3).
Figure 7B:
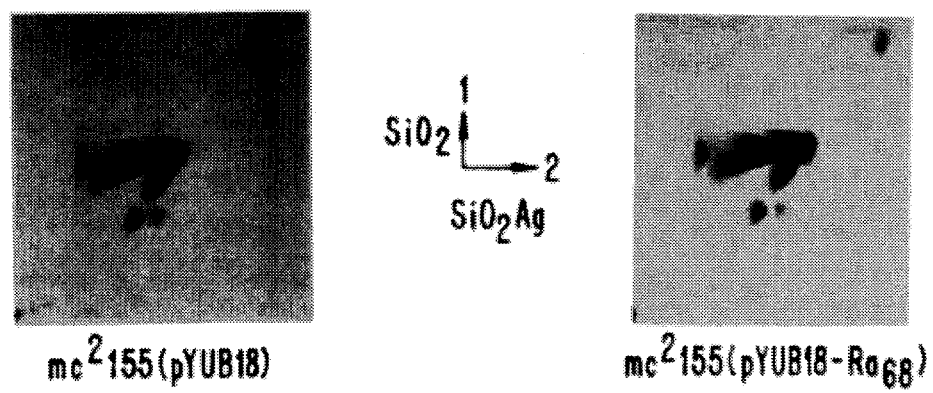

The purified mycolic acids were examined by thin-layer chromatography (TLC) on silica gel plates which had been treated with 5% silver nitrate. This argentation TLC process allows selective complexation of components which have cis double bonds with silver ions while components with no double bonds or cyclopropanes are unaffected in their mobility. D.A. Kennerly, *J. Chromatography* 363, 462(1986). As shown in FIG. 7, purified mycolic acids from H37Ra and *M. smegmatis* are clearly resolved on argentation plates but not on conventional silica plates (compare lanes labeled 1 and 2 in both halves of FIG. 7A). Of 697 clones which were screened, two had modified mycolic acids as judged by TLC (corresponding to cosmids pYUB18-Ra₆₈ and pYUB18-Ra₁₈₉). A clearer resolution of the new mycolates is shown in FIG. 7B where total mycolates were isolated from $^{14}$C-acetate labeled cultures containing either the parent cosmid (pYUB18) or one of the two cosmids containing inserts which conferred this phenotype (pYUB18-Ra₆₈). In these two-dimensional TLC analyses, about 90% of the plates were coated with silver and the samples were run in the first dimension along the narrow strip without silver impregnation and then turned 90° and run into the silver layer. This enhanced resolution reveals the true complexity of the *M. smegmatis* mycolic acids and clearly demonstrates the presence of a new mycolate whose mobility is unaffected by silver ion impregnation. In this two-dimensional system, the novel mycolate co-migrates exactly with the α-mycolic acid isolated from *M. tuberculosis* H37Ra.

Figure 8:
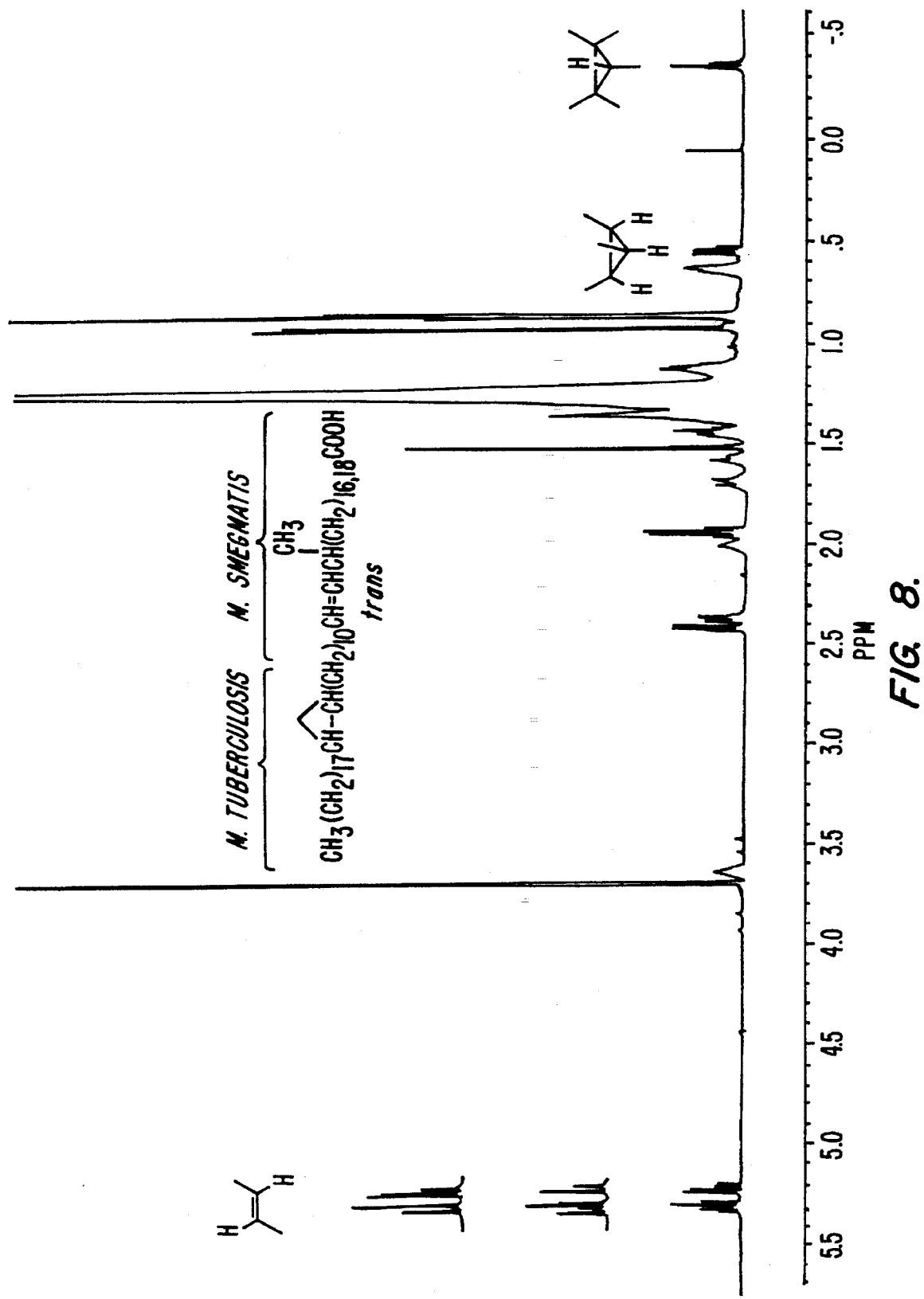
FIG. 8 shows an $^1$H-NMR spectrum of purified cyclopropanated mycolic acid methyl ester produced by the *M. smegmatis* clone of Example 1.

To further identify this novel mycolic acid, about 1 mg of this component was purified to homogeneity from 0.5 liter of mc²155 (pYUB18-Ra₁₈₉) by base hydrolysis, extraction and methylation followed by preparative TLC on silver plates. An examination of the 500 MHz¹H-NMR spectrum (FIG. 8) clearly shows resonances for the cyclopropyl ring hydrogens ($\partial 0.62$, $\partial 0.54$, $\partial 0.34$) as well as olefin resonances associated with the normal *M. smegmatis* major mycolate trans double bond ($\partial 5.32$, $\partial 5.22$, J=15.3 Hz). See, Wong, et al. 1979, *J. Biol. Chem.* 254, 5734(1970); Danielson, et al. *J. Biol Chem.* 257, 1 2196(1982). Decoupling experiments (lower offset in FIG. 8) demonstrated that the terminal methyl group at $\partial 0.92$ is adjacent to a methane at $\partial 2.00$ which is coupled to a vinyl proton at $\partial 5.22$. Decoupling the methylene $\partial 1.94$ revealed that it was adjacent to the vinyl proton at $\partial 5.32$ (upper offset in FIG. 8). The $^{13}$C NMR also supports this identification. The relative position of these two functional groups were established by mass spectrometry of pyrrolidide derivatives of fragments following cleavage of the purified mycolate with chromium trioxide. The presence of these functional groups in a single mycolate is consistent with the structure shown in FIG. 8 which is comprised of the normal *M. smegmatis* α-mycolic acid with the distal double bond having been cyclopropanated. NMR spectra of crude mixtures of mycolates from mc²155(pYUB18), mc²155(pYUB18-Ra₁₈₉) and mc²155(pYUB18-Ra₆₈) were also compared. Protons corresponding to the cyclopropane ring were only observed in significant quantities in the mycolates isolated from the two recombinant clones and corresponded to 14% and 19% by integration of the total mycolic acids.

Figure 4:
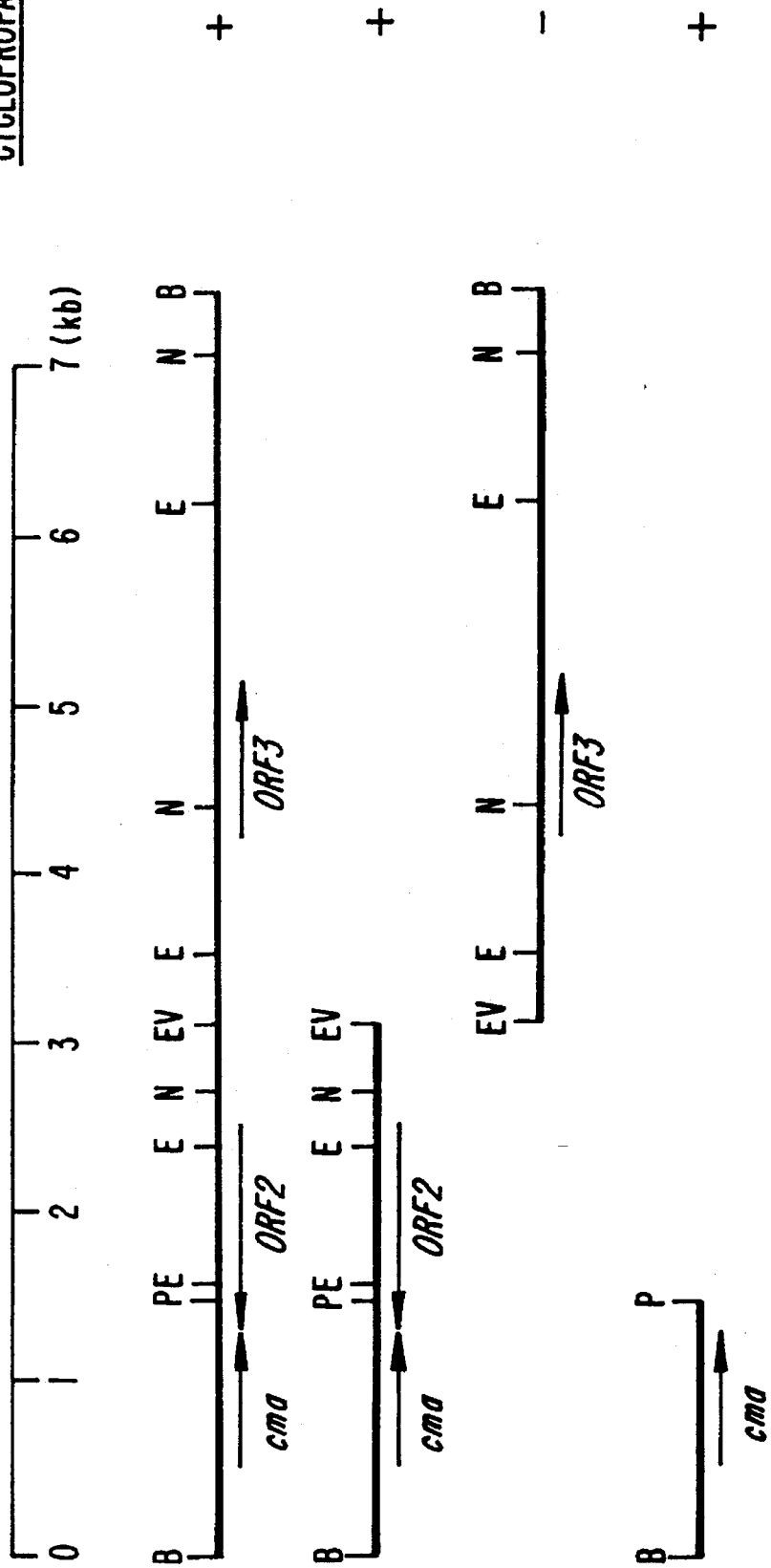
FIG. 4 is a restriction map for a 7.2 kb BamHI restriction fragment within which can be found the three isolated open reading frames of the present invention, namely cma, ORF 2 and ORF3 (SEQ. ID. Nos. 2, 4 and 6). This restriction map also illustrates the involvement of cma (SEQ. ID. No. 2) in the cyclopropanation of mycolic acids in *M. tuberculosis*, but the lack of any such involvement by ORF3 (SEQ. ID No. 6).

The two independent cosmid isolates which conferred this phenotype were separately isolated and used to retransform *M. smegmatis*, confirming that the activity was, in fact, encoded by these DNA sequences and had not arisen by spontaneous mutation. Restriction mapping these cosmids with BamHI produced fewer than ten fragments, three of which were common to both cosmids. BamHI fragments from the cosmid with fewer total BamHI fragments (pYUB18-Ra₁₈₉) were cloned into pYUB18 and transformants were again screened for the cyclopropanated mycolic acid phenotype. Two colony sizes were noted in these transformants. In the large colony phenotype, none of the twenty-four transformants had modified mycolic acids while in the small colony phenotype, four in twenty-four were positive. This result suggested that in *M. smegmatis*, cyclopropanation may result in a slower growth rate than *M. tuberculosis*. Cosmid DNA from these retransformants was isolated from all four of the colonies with modified mycolates and all four were found to contain a single 7.2 kb BamH I fragment. This fragment was common to both the initial cosmid isolates and was restriction mapped as shown in FIG. 4.

The 7.2 kb BamH I fragment was subcloned into a 3.1 kb BamH I to EcoR V and a 4.1 kb EcoR V to BamH I fragment and the cyclopropanation activity coincided with the smaller 3.1 kb fragment. This fragment was cloned in an orientation-independent fashion with BamH I linkers and twelve of twelve clones tested had cyclopropanated mycolates. This result suggests that this reading frame is operating from its own promoter. This fragment was further subcloned to a 1.51 kb BamH I to Pst I fragment which also conferred the ability to cyclopropanate mycolic acids. Subclones of this fragment were restriction mapped and inserts in both orientations tested positive for the cyclopropanation phenotype, again suggesting the presence of promoter sequences in this fragment, although no typical transcriptional or translational initiation signals were observed.

Example 2: Construction of Overexpression Vector For cma

An overexpression vector was constructed for the expression of the recombinant MACE protein (SEQ ID. No. 3) in Mycobacterial species. This vector was designed to incorporate features which maximize expression of MACE in mycobacteria and retain features which allow expression in the shuttle partner, *E. coli*. This vector was constructed in three steps: (1) construction of a promoter fragment bearing the hsp60 promoter sequence from *M. tuberculosis* H37Rv, (2) construction of a fusion system with multiple cloning sites, and (3) placement of the expression signals in a hygromycin shuttle plasmid called p16R1. The details of the overexpression vector are shown schematically in FIG. 5.

For construction of the promoter fragment, the following two primers were used to PCR amplify 257nt of upstream sequence from the *M. tuberculosis* H37Rv hsp60 gene: (1) 5'-GCCATATGCTTCTTGCACTCGGCATAG-3' (SEQ ID. No. 16), (2) 5'-CCATATGCATTGCGAAGTGATTCCTCC-3' (SEQ ID. No. 17). These primers were selected by reference to Thole et al., *Infection and Immunity*, 55, 1466–1475(1987). The resulting fragment was purified and cloned after cutting with XbaI and NdeI restriction enzymes.

A fusion system was then constructed with both a polylinker and poly-his tag system included in the cloning region of pRSET-B (Invitrogen Corp.). pRSET-B was double digested with XbaI and NdeI restriction enzymes and ligated to the digested promoter fragment. This construct was used as a template for an additional PCR amplification involving sequences which originated in pRSET and the mycobacterial promoter sequences. This cassette was PCR amplified using the following primers: (1) 5'-GGTCTA-GAGCTTCTTGCACTCG GCATAGGCG-3' (SEQ. ID No. 18) and (2) 5'-CCATATGCATTGCGAAGTGATTCCTCC-3' (SEQ. ID No. 19). The resulting modified promoter region was sequenced in this vector to produce the full nucleic acid sequence of SEQ. ID No. 20. The putative amino acid sequence for this full nucleic acid sequence is shown in SEQ. ID No. 21.

Figure 5:
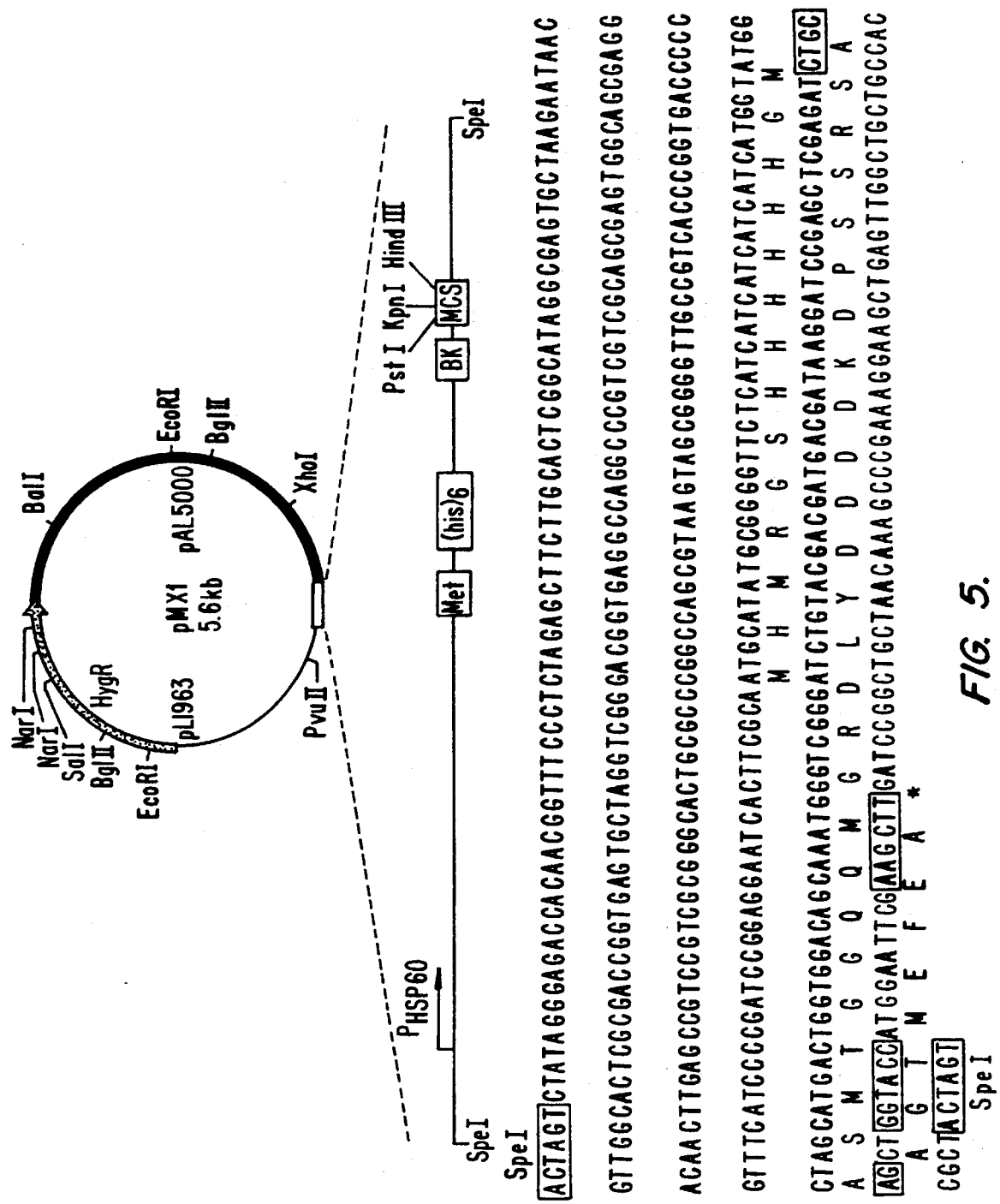
FIG. 5 shows how an overexpression system can be created in a pMX 1 vector to express MACE (SEQ. ID No. 3).

For construction of the hygromycin shuttle vector, a p16R1 vector was first digested with KpnI, filled by T4DNA polymerase, ligated with SpeI linkers and then digested with SpeI. The p16R1 vector is described in and available from Garbe et al., *Microbiology* 140, 133–138(1994). The DNA fragment of SEQ. ID No. 20 was then digested with SpeI restriction endonuclease and ligated to the specially prepared p16R1 vector. Inserts in both orientations were obtained and screened by restriction mapping. A full map of the resulting overexpression vector, called pMX1, is shown in FIG. 5.

Figure 6:
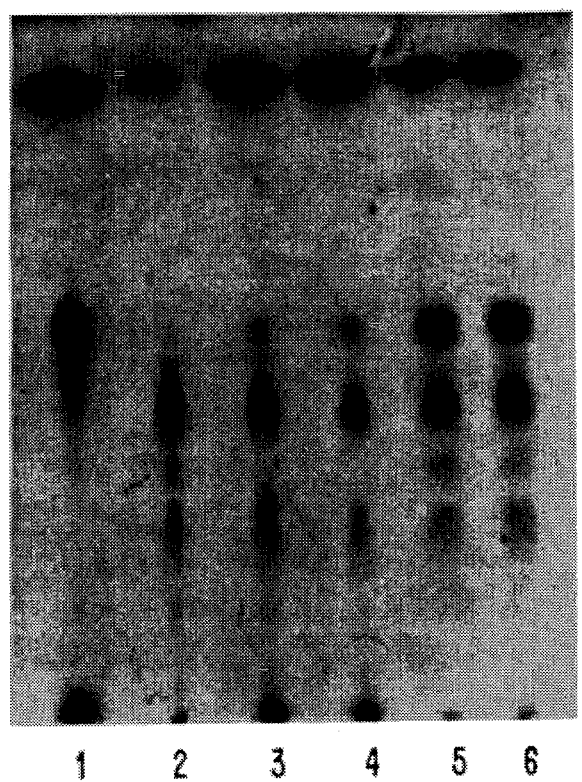
FIG. 6 shows a thin layer chromatography ("TLC") comparison of the MACE produced by the overexpression system of FIG. 5 with that produced by other systems.

After the overexpression vector pMX1 was prepared, the cma nucleic acid sequence (SEQ. ID No. 2), which encodes the MACE protein (SEQ. ID No. 3), was PCR amplified with the primers of SEQ. ID Nos. 10 and 11 and then cloned into the overexpression vector pMX1. FIG. 6 shows the TLC test results of the pMX1 overexpression vector with the cma gene in an *M. smegmatis* host. Lane 1 of this TLC shows *M. tuberculosis* H37Ra purified mycolic acids, Lane 2 shows mycolic acids isolated from wild type *M. smegmatis*, Lanes 3 and 4 show the level of expression from the cma promoter on the cosmid constructs in pYUB18, Lanes 5 and 6 show two isolates of cma cloned into pMX1. By comparing the various Lanes from this TLC, one can see that much more of the total mycolates are converted to the cyclopropanes from the clone in which the cma gene is expressed from the hsp60 promoter. Accordingly, this overexpression vector was found to be important because it allows the isolation and analysis of large quantities of MACE protein and provides a simple means for purification via the poly-his sequence on Invitrogen's metal affinity matrix.

Example 3: Direct Chemical Assay To Detect Inhibition Of MACE Activity

The effectiveness of a prospective therapeutic to inhibit cyclopropanation of mycolic acids in *M. tuberculosis* was assayed using the *M. smegmatis* clone described in Example 1. For this assay, fresh transformants of mc$^2$155 with cosmid or plasmid DNA expressing the cma gene were selected off 7H11 agar plates containing 25 µg/ml kanamycin and used to inoculate cultures in 7H9 media with OADC, 0.05% Tween 80 and the prospective therapeutic. These cultures were grown for 48–72 hours before removing 1 ml from each well for mycolate analysis. The 1 ml samples were transferred to PTFE capped vials and centrifuged at 1500 rpm for 10 minutes before aspirating the excess media. Toluene (1 ml) was added followed by a 1:1 mixture of methanol:30% aqueous potassium hydroxide (1 ml). The vials were sealed and heated for at least 12 hours at 75° C. After cooling on ice and adding 250 µl of concentrated hydrochloric acid, each sample was extracted with approximately 2 ml of diethyl ether. The aqueous layer was removed and the ether washed with 1 ml of distilled water which was also removed. The ether layer was evaporated under a stream of argon before adding dichloromethane (0.5ml), catalyst solution (0.5 ml) (sodium hydroxide, 0.8 g, tetrabutylammonium hydrogen sulfate, 3.39 g in 100 ml of distilled water) and methyl iodide (25 µl). The samples were allowed to sit with periodic vortexing for about an hour before the dichloromethane layer was removed to a microcentrifuge tube and evaporated. Toluene (200 µl) and acetonitrile (100 µl) were added to each sample and they were vortexed until the pellet redissolved. Acetonitrile (200 µl) was added to each sample and placed at 4° C. for two hours before spinning at 14,000 rpm for 10 minutes and removing the supernatant (11). The pellets were air-dried and then redissolved in a small volume (ca 20 µl) of benzene before spotting 0.5 µl onto TLC plates. Argentation TLC plates were eluted twice with 9:1 hexanes:ethyl acetate and developed by immersion in 10% sulfuric acid in ethanol followed by charring. Alternatively, two-dimensional TLC of recombinant cultures labeled overnight with $^{14}$C Acetate was performed as follows: 90% of a square plate is coated with silver and the samples are run in the first dimension along the narrow strip without silver impregnation and then turned 90° and run into the silver layer. The first dimension is run by eluting twice with 9:1 hexanes:ethyl acetate. The plates are removed, dried, turned 90° and eluted twice with 85:15 petroleum ether:diethyl ether and exposed to autoradiography film for two days.

Example 4: Radiochemical Assay To Detect Inhibition Of MACE Activity

In this example, crude cell-free extracts from the cma overexpressing strain described in Example 2 or a related construct in a strain of *E. coli* are used to determine the effectiveness of a prospective therapeutic to inhibit cyclopropanation of mycolic acids in *M. tuberculosis*. Cell-pellets from the *M. smegmatis* overexpression strain of Example 2 are grown in an appropriate media with hygromycin at 50 µg/ml. The *M. smegmatis* cell-pellets are then harvested by centrifugation and resuspended in 0.1M potassium phosphate, pH 7.5, at 0°–4° C. The bacteria are disrupted by bead-beating with 0.1 mm zirconia-silica beads for 2 minutes and the supernatant is then clarified by centrifugation at 150,000 g for 2 hr. The resulting supernatant is treated with solid ammonium sulfate to 40% of saturation and centrifuged at 10,000 g for 15 minutes. The protein pellet is redissolved in a minimal volume of 0.1M potassium phosphate, pH 7.5, and dialyzed against two changes of 100 volumes of the same buffer at 4° C. This crude extract can be assayed directly or purified further using a modification of the method for purifying the cyclopropane fatty acid synthase from *Escherichia coli* described in Taylor and Cronan, *Biochemistry* 18,3292–3300(1979). To implement the Taylor and Cronan method for further purification, ammonium sulfate purified MACE, 60% sucrose, and a suspension of lipid from wild type *M. smegmatis* are mixed to give a solution containing final concentrations of sucrose, MACE protein and lipid of 30% (w/v), 10 mg/l, and 4 mg/ml, respectively, in 50 mM phosphate buffer at pH 7.5. After incubation at 37° C. for 15 minutes, 4 ml of this mixture is centrifuged after applying an overlay of 0.5 ml 25% sucrose in phosphate buffer, 0.5ml 20% sucrose in phosphate buffer and 0.1 ml buffer alone. The tubes are centrifuged at 80,000 g for 2 hr and a band collected from the 20% sucrose layer contains the purified MACE. After removal of excess salt and lipid by dialysis, the MACE protein preparation is stored in the presence of 1 mg/ml sorbitan monolaurate liposomes.

To detect the prospective pharmaceutical's inhibition of MACE activity, this assay relies on radiochemical incorporation from labeled S-adenosyl-(L)-methionine. The assay mixture consists of 0.1 mg of lipid dispersion from wild type *M. smegmatis*, 2 µmol potassium phosphate, pH 7.5, [methyl-$^3$H]-S-adenosyl-L-methionine (25 µCi/µmol), 0.05 µmol, 0.1 unit of S-adenosyl-L-homocysteine hydrolase and an appropriate concentration of the prospective therapeutic. After incubation at 37° C. for 30 minutes, the reaction is worked up either by trichloroacetic acid precipitation or by methanolic base hydrolysis and then analyzed by separation of the lipid products as their methyl esters on either tlc or HPLC and assayed for radioactivity incorporation. Alternatively, a high throughput assay format such as a modified form of Scintillation Proximity Assay (SPA) utilizing hydrophobically derivatized beads could be adapted to such an assay. As another option, the crude reaction products can be absorbed to filter membranes and the radiolabeled substrate removed by hot trichloroacetic acid washes.

Example 5: Production Of Polyclonal Antibodies To MACE

Polyclonal antibodies are raised to the MACE protein using a protocol developed by Quality Controlled Biochemicals, Inc. of Hopkinton, Mass. In this protocol, peptides corresponding to sequences of the MACE protein are first synthesized, purified and prepared for injection into a laboratory animal, such as a rabbit, for the production of polyclonal antibodies to MACE. To the extent that such peptides have been synthetically prepared through Solid Phase Peptide Synthesis (SPPS), the N-α-protection is removed through Fmoc (9-Fluorenylmethoxy-carbonyl) chemistry. Briefly, the deprotection and cleavage schemes utilized in the Fmoc protocols rely upon removal of N-α-protection by mild base hydrolysis and cleavage/deprotection once synthesis is complete by TFA (trifluoroacetic acid). The MACE protein solution is then purified to 90% + using a Gilson automated HPLC system with UV detection at 215/280 nm and Vydac HPLC columns. The mobile phases for this protocol are HPLC-grade $H_2O$ and acetonitrile, both with 0.1% TFA. Purity and size of MACE peptides are verified by mass spectrometric analysis using a Vestec Electrospray Mass Spectrometer. To enhance its effectiveness in raising antibodies in the rabbit subjects, the MACE protein is coupled to keyhole limpet hemocyanin (KLH, MW=$3 \times 10^6$) and crosslinked with MBS (m-maleimidobenzoyl-N-hydroxysiccinimide).

The protocol for injecting the purified, coupled MACE peptide antigen into rabbits and harvesting the antibodies raised against MACE spans a period of 120 days. On Day 0, a preimmune sample (2–3 ml) is taken from the ear vein of the rabbit prior to injection of the MACE antigen. Coupled MACE-peptide, suspended in PBS (phosphate buffered saline) at 1 mg/ml, is mixed with an equal volume of complete Freund's adjuvant. This material is mixed until it forms an emulsion and then is injected at 6–8 subcutaneous sites. A total of 150–200 µg of MACE-peptide is injected. On Day 14, the same emulsion is injected into the rabbits as Day 0. On Day 35, the MACE-peptide is mixed with Incomplete Freund's antigen and the resulting emulsion is injected (150 µg MACE-peptide) at 6–8 subcutaneous sites. On Day 45, a test bleed (10–15 ml of serum) is taken from the auricular artery of the rabbit. On Day 55, the MACE-peptide antigen is again mixed with Incomplete Freund's antigen and the resulting emulsion is injected (150 µg MACE-peptide) at 6–8 subcutaneous sites. On Days 80 and 85, production bleeds (20–25 ml of serum per rabbit) are taken from the auricular artery. On Day 105, the MACE-peptide antigen is mixed again with Incomplete Freund's antigen and the resulting emulsion is injected (150 µg MACE-peptide) at 6–8 subcutaneous sites. Finally, on days 115 and 120, production bleeds (20–25 ml of serum per rabbit) are again taken from the auricular artery.

An affinity purification of the specific antibody from production bleeds is performed using the SulfoLink kit made by Pierce Chemical Company of Rockford, Ill. In using this kit, the SulfoLink gel is first washed with phosphate-buffered saline (PBS) followed by the addition of 1.2 to 1.5 mg of MACE-peptide per ml of resin. After allowing the gel and peptide to react, the gel is washed extensively and a solution of 50mM cysteine is incubated with the gel to react with any remaining functional groups. The column is then washed again and is ready for exposure to serum. It is noteworthy that the highest yields of antibody are obtained when the column material is removed from the column and mixed with 20 ml of serum and 20 ml of PBS in a 50 ml conical. After 2–3 hours of room temperature incubation on a rocker or an overnight incubation at 4° C. with agitation, the serum and gel are poured back into the Econo column and the serum flow-through frozen. The column is then washed with phosphate buffer containing 250–500 mM NaCl until no protein is eluted and the column exposed to 100 mM glycine buffer, pH 2.5. 1 ml fractions are then collected into tubes containing 50 µl of 1M Tris-Hcl, pH 9.5, to immediately neutralize the pH and protect the integrity of the antibody. The fractions containing antibody are usually visible due to their opaque nature or they can be identified by measuring the $A_{280}$ of selected fractions. This opaque material is pooled and dialyzed for 20–24 hours using a 10,000 MWCO dialysis membrane, such as that manufactured by SpectraPor, in 4 liters of 5 mM phosphate buffer pH 7.4, changing the buffer after a few hours and again the next morning. The resulting material is then lyophilized for long-term storage.

In the foregoing specification, the invention has been described with reference to specific exemplary embodiments. It will, however, be evident that various modifications and changes may be made without departing from the broader spirit and scope of the invention as set forth in the appended claims. Many such changes or modifications will be readily apparent to one of ordinary skill in the art. The specification and drawings are, accordingly, to be regarded in an illustrative rather than a restrictive sense, the invention being limited only to the provided claims.

What is claimed is:

1. A method to determine the ability of a compound to inhibit the cyclopropanation of mycolic acids in pathogenic mycobacteria comprising the steps of:

(a) contacting said compound with a composition capable of producing cyclopropanated mycolic acids; and (b) detecting changes in mycolic acid cyclopropanating enzyme (MACE) activity and thereby determining the ability of said compound to inhibit the cyclopropanation of mycolic acids in pathogenic myobacteria.

2. The method of claim 1 wherein said composition capable of producing cyclopropanated mycolic acids includes partially or completely purified MACE.

3. The method of claim 1 wherein the composition capable of producing cyclopropanated mycolic acids includes *Mycobacterium tuberculosis*.

4. The method of claim 1 wherein said composition capable of producing cyclopropanated mycolic acids includes recombinant *M. smegmatis* which expresses MACE.

\* \* \* \* \*